US008384046B2

(12) United States Patent
Haidekker et al.

(10) Patent No.: US 8,384,046 B2
(45) Date of Patent: Feb. 26, 2013

(54) NON-INVASIVE METHODS AND APPARATUS FOR DETECTING INSECT-INDUCED DAMAGE IN A PLANT

(75) Inventors: Mark A. Haidekker, Athens, GA (US); Michael D. Toews, Tifton, GA (US); Jinjun Xia, Seattle, WA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 30 days.

(21) Appl. No.: 13/146,489

(22) PCT Filed: Jan. 29, 2010

(86) PCT No.: PCT/US2010/022491
§ 371 (c)(1),
(2), (4) Date: Aug. 24, 2011

(87) PCT Pub. No.: WO2010/088452
PCT Pub. Date: Aug. 5, 2010

(65) Prior Publication Data
US 2011/0297848 A1 Dec. 8, 2011

Related U.S. Application Data

(60) Provisional application No. 61/206,484, filed on Jan. 30, 2009.

(51) Int. Cl.
*G01N 21/64* (2006.01)
(52) U.S. Cl. ................... 250/459.1; 250/458.1
(58) Field of Classification Search ................ 250/459.1
See application file for complete search history.

(56) References Cited

U.S. PATENT DOCUMENTS

| | | | |
|---|---|---|---|
| 4,535,248 A | 8/1985 | Schade et al. | |
| 4,866,283 A | 9/1989 | Hill | |
| 5,822,068 A * | 10/1998 | Beaudry et al. | 356/417 |
| 2004/0130714 A1 | 7/2004 | Gellerman et al. | |
| 2006/0102851 A1 | 5/2006 | Jalink | |

OTHER PUBLICATIONS

International Search Report and Written Opinion, dated Sep. 10, 2010.

* cited by examiner

*Primary Examiner* — Marcus Taningco
(74) *Attorney, Agent, or Firm* — Thomas, Kayden, Horstemeyer & Risley, LLP

(57) ABSTRACT

Lesions caused by insects feeding on plants are associated with the generation of regions of blue-green fluorescence in such as the cotton boll carpel wall and in the lint region. The present disclosure now provides methods and devices to rapidly and non-invasively detect and measure the insect-related fluorescence and relate the fluorescence generated to the likelihood of insect damage in a crop. In particular, the methods are related to stink bug damage in the cotton plant, but are also suitable for the detection of insect-related damage of any plant. The methods of detecting insect-induced damage in a target plant tissue may comprise exposing a target plant or a fragment thereof, to an ultraviolet or violet light; and detecting an ultraviolet light-induced fluorescence from the target plant or the fragment thereof, thereby indicating the presence of insect-related plant damage. Further provided are devices configured for the identification of insect-induced damage in a plant or a fragment thereof, comprising: a source of an ultraviolet or violet light, at least one light detector; an electronic system for converting an output electrical signal to a measurement of the intensity of fluorescent light detected by the detector; and an output system to convert the measurement of the intensity of the fluorescent light to an indicator for indicating that a target plant or fragment thereof has insect-induced damage.

17 Claims, 18 Drawing Sheets

NON-INVASIVE METHODS AND APPARATUS FOR DETECTING INSECT-INDUCED DAMAGE IN A PLANT

CROSS REFERENCE TO RELATED APPLICATION

This application claims priority to "NON-INVASIVE METHODS AND APPARATUS FOR DETECTING INSECT-INDUCED DAMAGE IN A PLANT" having serial number PCT/US2010/022491, filed on Jan. 29, 2010. This application also claims priority to and benefit of U.S. Provisional Application No. 61/206,484, filed on Jan. 30, 2009, which is incorporated by reference in its entirety.

TECHNICAL FIELD

The present disclosure is generally related to methods and devices for the non-invasive detection of insect-generated damage of a plant.

BACKGROUND

Cotton production in U.S. has undergone profound changes in the last two decades. For example, the successful eradication of the boll weevil and deployment of Bt-transgenic cotton have helped increase Georgia's cotton acreage from 125,000 acres in 1996 to more than 1 million acres. In addition, pest management advancements have helped reduce chemical insecticide applications from more than 15 per year in 1996 to less than 3 in 2007. However, the insect pest complex has also changed and previously unimportant insect pests like stink bugs now threaten productivity and fiber quality.

Stink bug damage to developing cotton bolls has recently been directly linked to decreased cotton fiber quality. Stink bugs damage developing cotton bolls by piercing the boll wall and feeding on the developing seed. In addition to physical damage to the seed (the fiber is part of the seed), pathogens may also be introduced during feeding or enter the boll through insect-induced wounds causing individual locks or the entire boll to rot and be unharvestable. Yield losses from bug damage to bolls have been documented in various studies (Cassidy & Barber (1939) *J. Econ. Entomol.* 32: 99-104; Toscano & Stern (1976) *J. Econ. Entomol.* 69: 53-56; Barbour et al., (1990) *J. Econ. Entomol.* 83: 842-845; Greene et al., (2001) *J. Econ. Entomol.* 94: 403-409). In no-choice feeding studies, stink bugs reduced seed cotton yield in bolls that had accumulated less than 550 heat units (Greene et al., (2001) *J. Econ. Entomol.* 94: 403-409; Willrich et al., (2004) *J. Econ. Entomol.* 97: 1928-1934). Relatively few studies have examined influences of boll feeding bugs on fiber quality (Toscano & Stern (1976) *J. Econ. Entomol.* 69: 53-56; Barbour et al., (1990) *J. Econ. Entomol.* 83: 842-845). Stink bugs prefer to feed on bolls ranging in age from 7-27 days after anthesis (Willrich et. al., (2004) *J. Econ. Entomol.* 97: 1928-1934), although some recent data show bolls only 3-4 days after white flower were most susceptible to shedding and stink bug injury. Cotton fibers develop to maturity within approximately 45 days of anthesis. Fiber elongation, measured as staple length, occurs during the first 3 weeks following anthesis, while fiber deposition or thickening, measured by micronaire, occurs during the second 3 weeks of boll development.

A number of phytophagous stink bugs, including the southern green stink bug, *Nezara viridula*, the green stink bug, *Acrosternum hilare*, and the brown stink bug, *Euschistus servus* have become serious pests of cotton production. These pests pose difficult management challenges because of limited information on basic ecology, distribution within fields and across the farmscape, and a lack of management tactics other than chemical control. There is also evidence that stink bugs are active flyers and frequently move among adjacent crops in the farmscape. Stink bugs have more than 200 known host plants (agronomic and nonagronomic plants).

Stink bugs are robust insects that use their piercing-sucking mouthparts to remove plant fluids from squares and bolls and can damage even relatively mature cotton bolls. Affected bolls then develop small sunken black spots on the outside surface. Internal evidence of feeding may be seen when bolls are opened by hand and lint, seeds, and carpel walls are examined for signs of feeding injury. The seeds and lint usually turn brown as a result of stink bug feeding. Wart-like callus growths may be present on internal carpel walls, marking the feeding wounds and the plant's response to injury.

Infestations are highly aggregated within a single field. A commonly employed method of determining if a crop field has a stink bug infestation involves the use of a drop cloth. Using this method, sample plants are vigorously shaken over a white cloth and the dislodged insects are enumerated. Typically, a few bolls are opened and inspected for signs of stained lint and internal injury. These methods, however, are time-consuming, may result in mechanical damage to the plants, and the drop-cloth method gives a count of the insects present, but not an indication of the extent of the damage to the plant tissues. Furthermore, development of cotton lint and seed damage may not be externally apparent even though the insects had pierced the boll. The grower may then incorrectly conclude that the crop was free of insect damage, allowing the pest to be untreated.

SUMMARY

It has been shown that piercing/sucking insects induce plant damage that results in blue-green fluorescence when the damaged tissues are viewed under ultraviolet or violet light exposure. In cotton, this fluorescence on the inner carpel wall and lint region is sufficiently intense to be detected by the unaided eye. The present disclosure provides methods and devices to non-invasively detect and measure the insect-related fluorescence and relate the fluorescence generated to the likelihood of insect damage in a crop. In particular, the methods are related to stink bug damage in the cotton plant, but are also suitable for the detection of insect-related damage of any plant.

One aspect of the disclosure, therefore, encompasses methods of detecting insect-induced damage in a target plant tissue, comprising: (a) exposing a target plant or a fragment thereof to an ultraviolet or violet light; and (b) detecting a first ultraviolet or violet light-induced fluorescence from the target plant or the fragment thereof, where a detectable level of fluorescence indicates the presence of insect-induced damage to the target plant or the fragment thereof.

In various embodiments of the disclosure, the method further comprises: (i) detecting a second ultraviolet or violet light-induced fluorescence from the target plant or the fragment thereof; (ii) measuring the levels of the intensities of the first fluorescence and the second fluorescence; and (iii) determining the ratio of the level of intensity of the first ultraviolet or violet light-induced fluorescence to the level of the intensity of the second ultraviolet or violet light-induced fluorescence; whereby said ratio indicates the level of insect-damage to the plant or the fragment thereof.

In embodiments of this aspect of the disclosure, the target plant may be selected from the group consisting of: a leguminous crop, a grass crop, and a fruiting body crop.

In embodiments of this aspect of the disclosure, the target plant can be selected from the group consisting of: soybean, cowpea, corn, sorghum, rice, wheat, alfalfa, pecan, macadamia, apple, pear, cotton, and tomato, or a hybrid or variety thereof.

In some embodiments of this aspect of the disclosure, the target plant is selected from the group consisting of: a cotton plant, a sunflower plant, and a soybean plant.

Another aspect of the disclosure encompasses devices configured for the identification of insect-induced damage in a plant or a fragment thereof, comprising: a source of an ultraviolet or violet light, wherein the wavelength thereof is selected to induce a fluorescence associated with insect-induced damage of a plant tissue; at least one light detector configured to provide an output electrical signal in response to a fluorescent light having a peak wavelength of about 405 nm to about 675 nm; an electronic system for converting the output electrical signal of the detector to a measurement of the intensity of the fluorescent light detected by the detector; and an output system for converting the measurement of the intensity of the fluorescent light detected by the detector to an indicator for indicating that a target plant or fragment thereof has insect-induced damage.

In embodiments of the apparatus of this aspect of the disclosure, the apparatus may further comprise an enclosure configured to receive a plant or a fragment thereof, and further configured to reduce ambient light around the plant or fragment thereof.

In embodiments of this aspect of the disclosure, the source of an ultraviolet or violet light and the at least one light detector are disposed as a linear array, and wherein the apparatus is configured to allow the linear array to rotate around the axis of the target plant or fragment thereof.

In one embodiment of this aspect of the disclosure, the source of an ultraviolet or violet light is configured to provide an ultraviolet or violet excitation light having a peak wavelength of about 365 nm, and the detector is configured to detect a first ultraviolet or violet light-induced fluorescence having a peak wavelength of about 405 nm, and a second ultraviolet or violet light-induced fluorescence may have a peak wavelength of about 465 nm, and the target plant is a cotton plant, or a fragment thereof.

In another embodiments of this aspect of the disclosure, the source of an ultraviolet or violet light is configured to provide an ultraviolet or violet excitation light having a peak wavelength of about 405 nm, and the detector is configured to detect a first ultraviolet or violet light-induced fluorescence having a peak wavelength of about 465 nm, and a second ultraviolet or violet light-induced fluorescence having a peak wavelength of about 515 nm, and the target plant is a sunflower plant, or a fragment thereof.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 9A: intact boll image; FIG. 9B: open boll image; FIG. 9C: stained lint image (left: lint; right: a crack boll); and FIG. 9D: less severe boll stain image:

Figure 1:
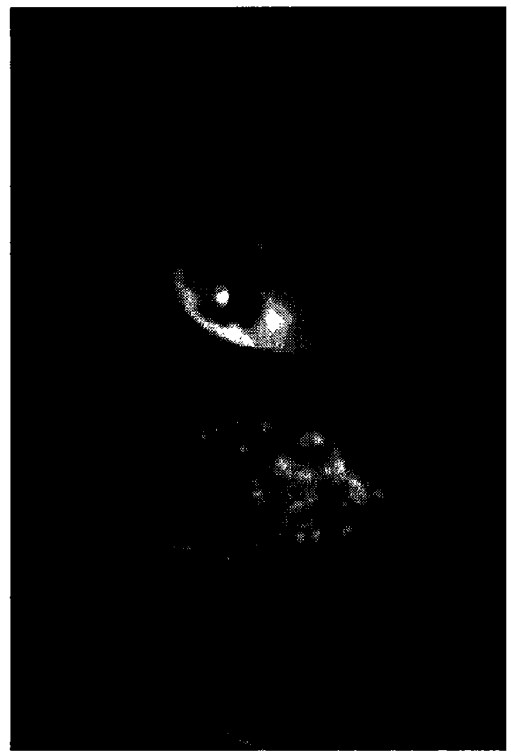
FIG. 1 shows digital camera images of the exposed inner carpel wall and the lint area of a cotton boll under long peak wavelength ultraviolet excitation. Left image: The carpel wall shows circular areas of blue-green fluorescence wherever a stink bug has pierced the carpel wall. Lint opposite the heaviest damage in the carpel wall (left image) also exhibits bright fluorescence. Right image: Included is a non-damaged carpel wall section that does not show the characteristic blue-green fluorescence.
Figure 1:
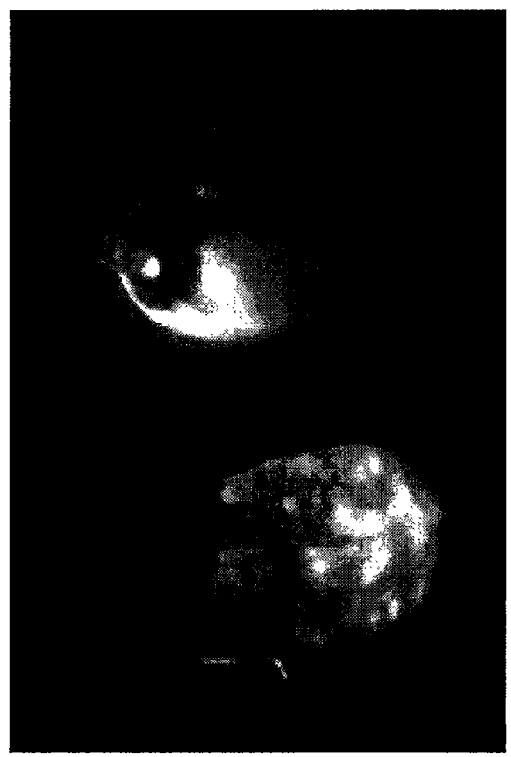

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

It is intended that the term "about" as applied herein to a peak wavelength of light may provide a range of peak wavelengths extending from about 5 nm below a peak wavelength to about 5 nm above a peak wavelength. For example, "a peak wavelength of about 365 nm" may refer to the range of from about 360 nm to about 370 nm.

The term "plant" as used here may refer to any plant, including, but not limited to, a crop plant or a wild plant. The term may further include any mono- or dicotylendous plant subject to insect damage. Such plants include, but are not limited to, legumes, grass-based crops including cereal plants and fruit crops. Crop plants may include, but are not limited to, a soybean, cowpea, corn, sorghum, rice, wheat, alfalfa, pecan, macadamia, fruit crops (such as, but not limited to, apples and pears), cotton, and tomato, or any other plant species, variety and the like that may be susceptible to damage by an insect including, but not limited to, a stink bug species.

The term "insect" as used herein refers to an insect that can induce a change in a tissue of a plant that may result in a shift of fluorescence peak wavelength, or a decrease in the intensity of fluorescence in the plant tissues. The term "insect" as used herein may refer to any phytophagous insect of the order Hemiptera, suborder Heteroptera, including, but not limited to, the superfamily Pentatomoidea, and including, but not limited to, the species green stink bug (*Acrosternum hilare*), brown stink bug (*Euschitus servus*), southern green stink bug (*Nezara viridula*) green shieldbug (*Palomena prasina*), brown marmorated stink bug (*Halyomorpha halys*), horehound bug (*Agonoscelis rutila*), forest bug (*Pentatoma rufipes*), and the like as described, for example, by Triplehorn & Johnson. (2005) in Borror & DeLong: Introduction to the Study of Insects, 7th Ed. Pub: Brooks/Cole, a Division of Thomson Learning, Inc. Belmont, Calif. (pp 864). The term may further relate to any piercing or biting insect that may cause or induce tissue damage to a plant, in particular economically valuable crop plants.

The term "ultraviolet or violet light" as used herein refers to a light having a peak wavelength of about 280 nm to about 405 nm, preferably about 340 nm to about 400 nm, and more preferably about 355 nm to about 380 nm.

DESCRIPTION

The present disclosure encompasses fluorescence-based methods, and provides embodiments of devices intended to apply said methods, for detecting insect-induced damage in plants. The methods of the disclosure are non-invasive and provide a rapid means for the detection of insect-induced damage to a plant by detecting an emitted fluorescence that correlates to the penetration of the plant tissues, by the mouth parts of insects such as, but not limited to, members of the stink bug group.

With established methods of assessing the presence of stink bugs in a cotton crop, developing cotton bolls are manually examined by splitting open to visually determine whether there is any discoloration or other damage to the cotton lint or the inner surface of the boll carpels. The main disadvantages of these methods are that they are time-consuming and depend on there being defects in the cotton lint or tissues that are attributable to insects and visible to the naked eye. Accordingly, these methods are only suitable for detecting insect infestations of a crop field that have had sufficient time from initial penetration of the boll tissue for the underlying damage to develop. Not readily detectable, if at all, is insect activity that has resulted only in the piercing of the plant tissue by the mouth parts, and for which there has not been sufficient time lapsed for tissue damage to form. The practical options for the grower who relies solely on manual examination of bolls is that crop insecticidal spraying may be delayed until the damage becomes apparent, during which time even more of the crop can be attacked. Alternatively, out of caution, the grower may resort to unnecessary spraying when the infestation was merely localized in the field. The time and labor for manual examination of a crop can also reduce the area of a crop field subject to checking, thereby failing to detect a localized insect activity, and underestimating the extent of any infestation.

Figure 15B:
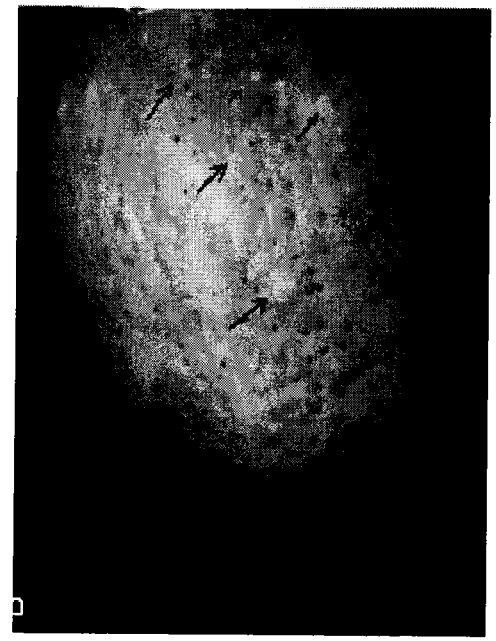
FIGS. 15A and 15B are digital images of an undamaged cotton boll (FIG. 15A) and cotton boll with stink bug damage (FIG. 15B), photographed under 390 nm ultraviolet excitation. Feeding spots show indicated by arrows in FIG. 15B.
Figure 15A:
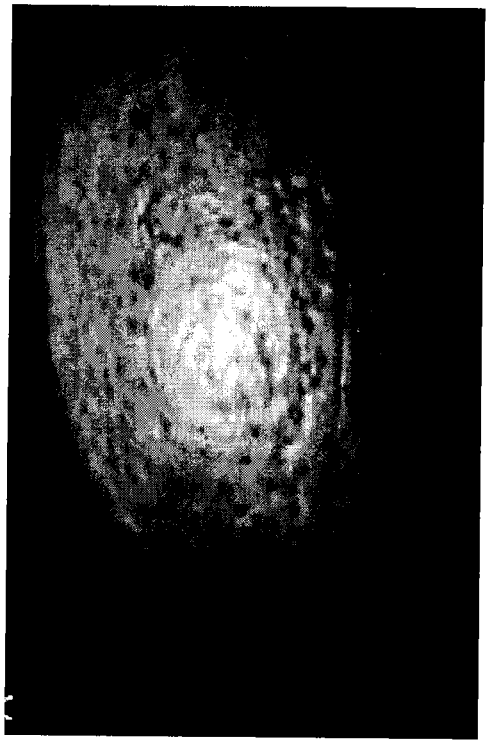

The methods of the disclosure detect ultraviolet and violet light-induced fluorescence at sites of tissue piercings of insects, and especially of the fluorescence emitted at or near the outer surface of the plant tissue at the site of penetration. The methods and related devices may be readily adapted for the rapid assessment of the extent of crop insect damage and avoid having to manually open parts of the plant to visually detect damage. The methods of the disclosure are able to detect an insect attack even though insufficient time may have elapsed for more extensive underlying tissue damage to have occurred. Thus, as shown in FIGS. 15A and 15B, for example, stink bug penetration of cotton bolls is detectable by blue-green fluorescence at the surface of developing bolls.

Figure 3:
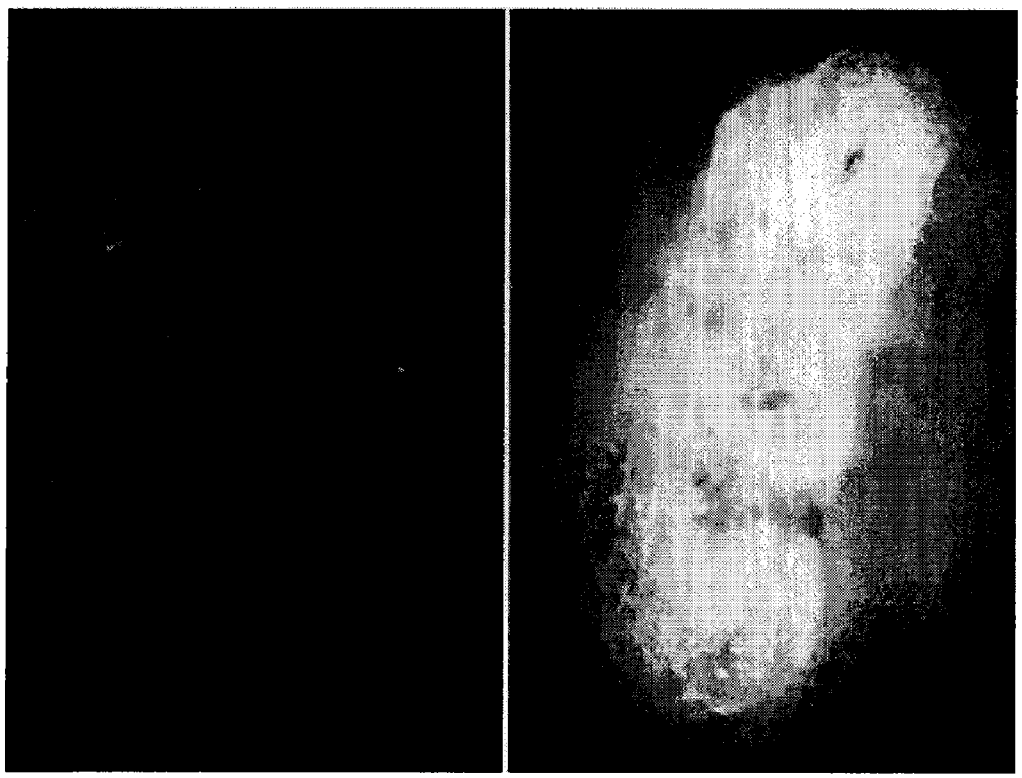
FIG. 3 shows digital epifluorescent microscope images of the inner carpel wall of an intact cotton boll (top) and a damaged cotton boll (bottom). Red chlorophyll emission dominates the intact boll, while the damaged boll predominantly exhibits blue-green fluorescence as shown in FIG. 1.

With the cotton boll, for example, it has been found that stink bug damage to the plant tissues is associated with a visible blue-green fluorescence. The blue-green fluorescence is typically restricted to small circular areas centered on the actual stink bug piercing hole in the inner carpel wall, as shown in FIG. 3. Near areas of high stink bug damage, the underlying lint may also show this characteristic blue-green fluorescence. This fluorescence can be detected and documented. Spectral analysis of the blue-green fluorescent regions exhibits a characteristic emission peak at about 460 nm.

Figure 2:
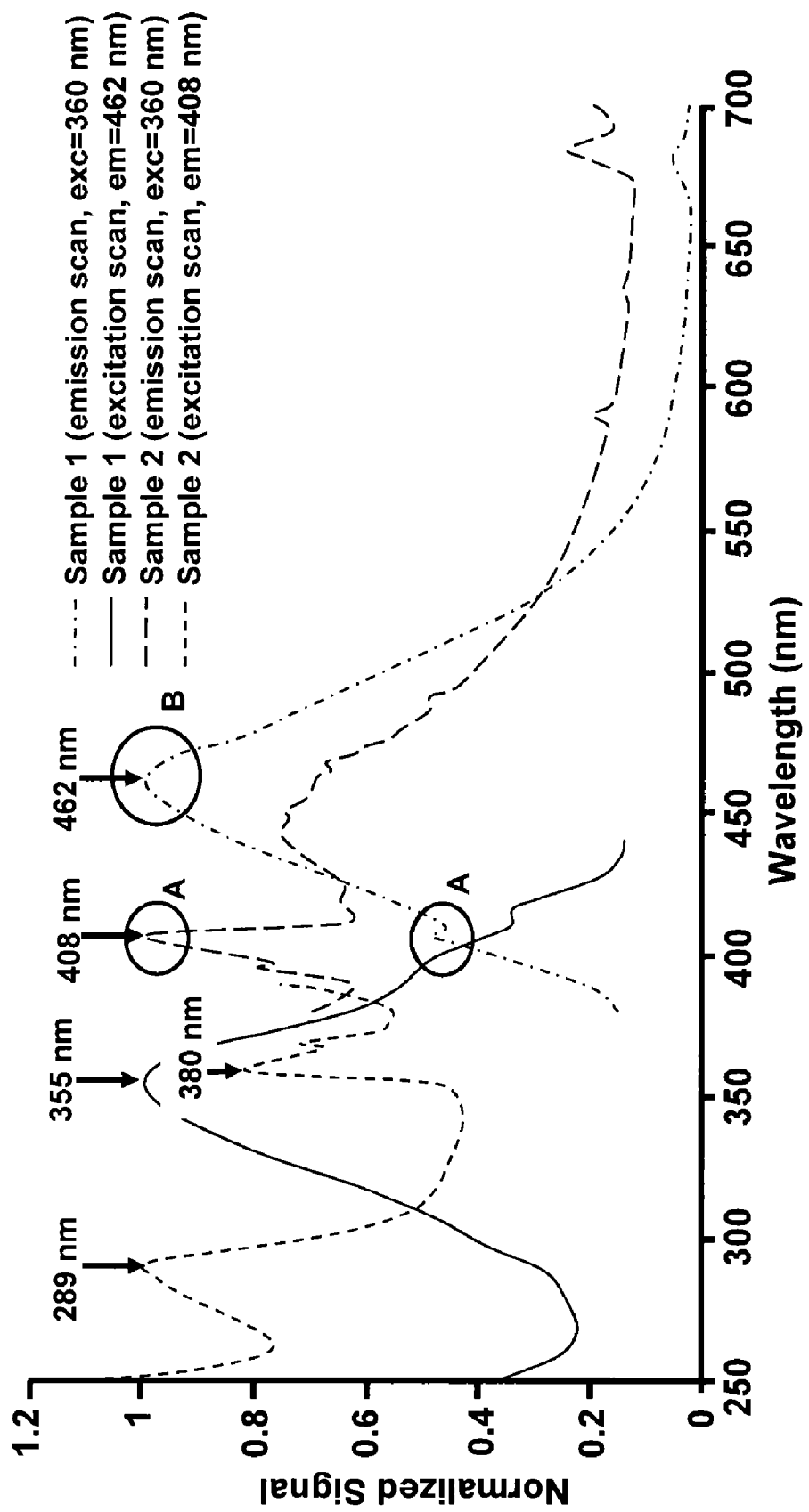
FIG. 2 illustrates the excitation and emission spectra of a section of a cotton inner carpel wall in the presence (Sample 1) and absence (Sample 2) of stink bug damage. Under ultraviolet excitation, the carpel wall tissue emits violet light at about 405 nm (circles labeled A). In the presence of stink bug damage, a much more intense peak at about 462 nm can be observed (circle labeled B). This emission peak is indicative of insect damage.

Referring to the figures, FIG. 2 shows excitation and emission spectra of a damaged (sample 1) and undamaged (sample 2) carpel wall. Under ultraviolet excitation at a peak wavelength of about 360 nm, undamaged cotton bolls emit violet fluorescence with a peak emission around about 405 nm (circles labeled A in FIG. 2). In the presence of stink bug damage, however, and again with ultraviolet excitation at a peak wavelength of about 360 nm, a much stronger emission peak at about 462 nm is seen (circle labeled B in FIG. 2). This peak at about 462 nm corresponds to the visually observed blue-green fluorescence visible in FIG. 1. The observation of the presence of an undamaged tissue-specific emission at about 405 nm, and an insect damage-specific emission at about 462 nm, allows a ratiometric measurement method of the extent of plant tissue damage. Under ultraviolet excitation, emission at both about 405 and about 462 nm can be observed simultaneously, and if the ratio of emissions exceeds a certain threshold, insect damage can be assumed.

The spectral data of FIG. 2 are further supported by images taken on an epifluorescent microscope under about 405 nm excitation. In this instance, the filter set can allow observation of chlorophyll fluorescence, which constitutes a third fluorescent component not included in the spectral images shown in FIG. 2. Microscope images of the inner boll wall are shown in FIG. 3. In FIG. 3, the top image shows a cotton boll that is free of insect damage. The image is dominated by a red chlorophyll fluorescence which is diffuse because it has been scattered by the carpel wall cell layer. The bottom images show an inner boll wall where insect piercing damage was observed. This image is dominated by blue-green fluorescence in the vicinity of the insect punctuation. This image corresponds to the macroscopic images shown in FIG. 1.

Figure 4:
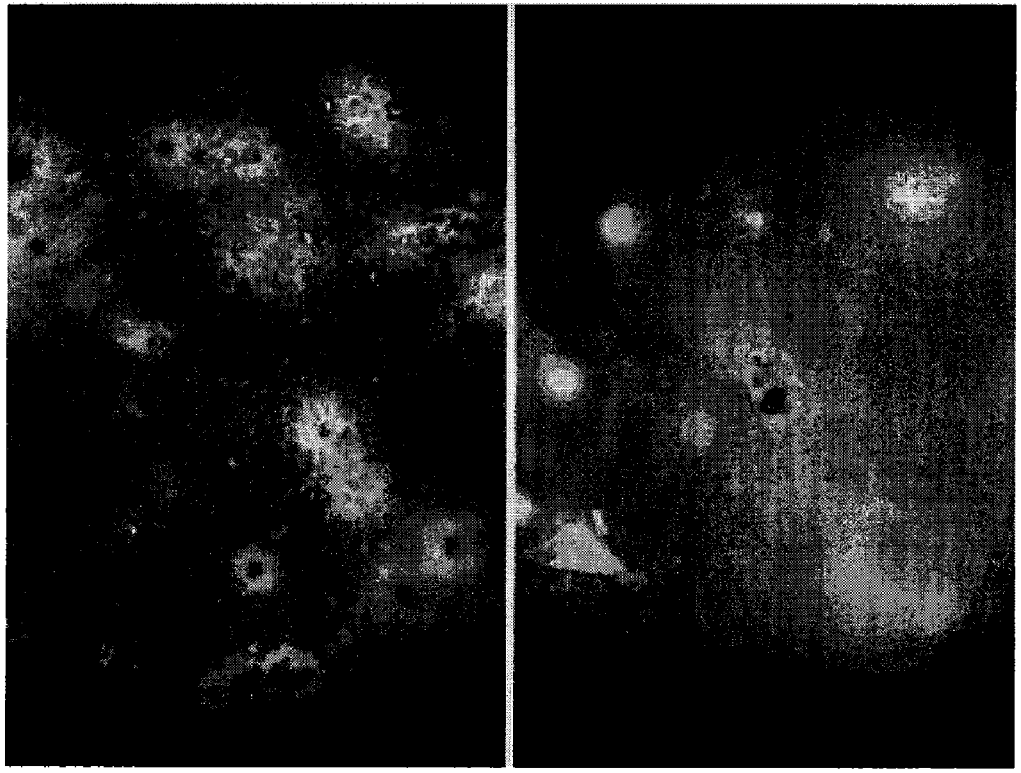
FIG. 4 shows digital epifluorescent photomicrographic images of the outer carpel wall of an intact cotton boll (top) and a damaged cotton boll (bottom). Red chlorophyll emission dominates the intact boll, although small patches of reduced chlorophyll emission are present. The damaged boll (the insect puncture site can clearly be seen) shows receding red chlorophyll emission in the presence of the characteristic blue-green component.

FIG. 4 shows the corresponding images taken of the outer carpel wall. In the intact boll not subject to insect attack (FIG. 4, top), the outer wall, too, is dominated by red chlorophyll emission. The boll with insect damage (FIG. 4, bottom) clearly shows the puncture site, the blue-green emission associated with insect damage, and receding red chlorophyll emission. The behavior of chlorophyll (namely its absence near the damage sites) provides a supplementary to the usual approach to obtaining a ratiometric spectroscopic measurement to determine the extent of insect damage.

Figure 5:
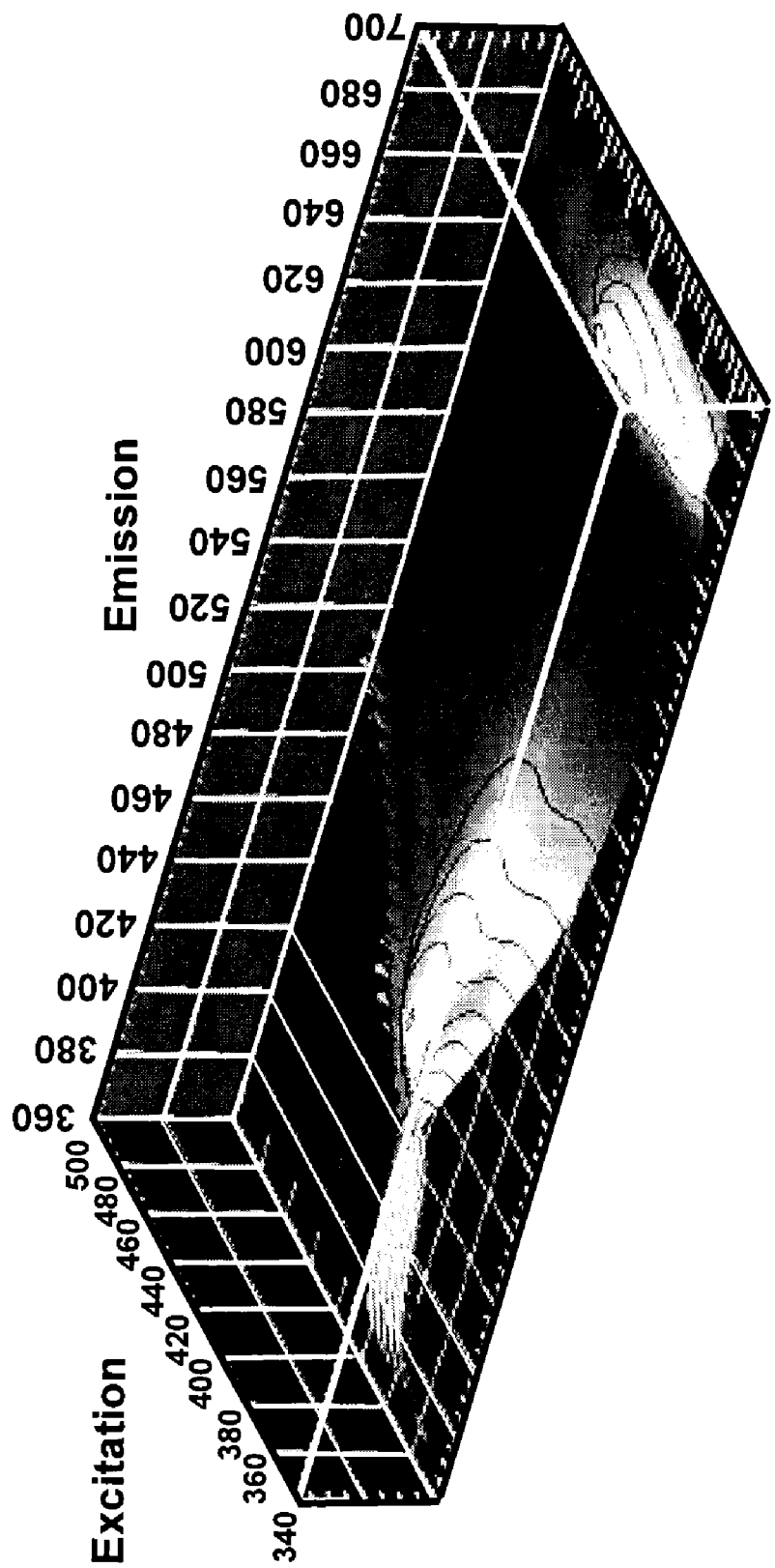
FIG. 5 shows a fluorescence fingerprint (matrix scan) of undamaged, intact cotton plant tissue. Green plant tissue shows predominantly chlorophyll fluorescence with 410 nm excitation and 675 nm emission.
Figure 6:
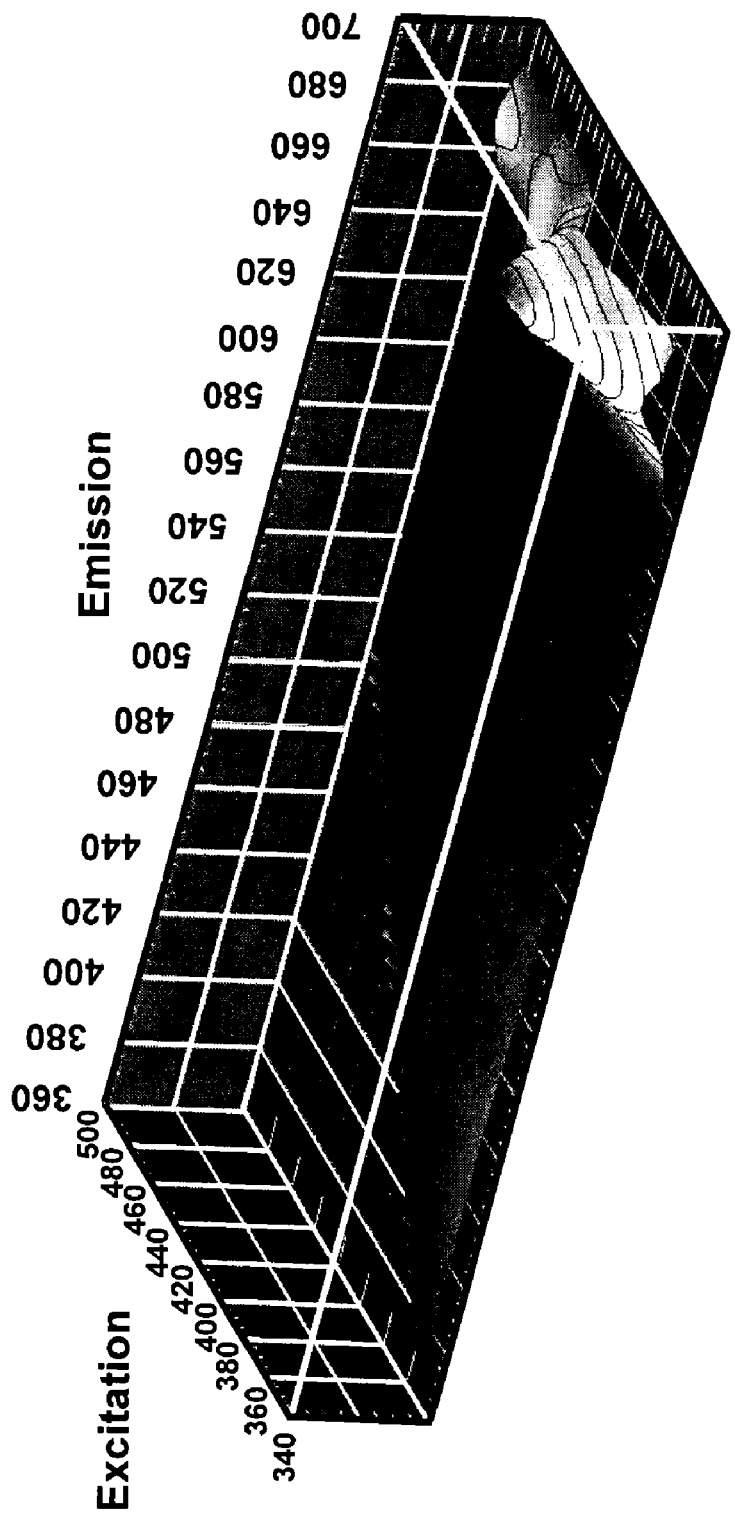
FIG. 6 shows a fluorescence fingerprint (matrix scan) of insect-damaged, intact cotton plant tissue. The chlorophyll auto-fluorescence peak shown in FIG. 5 is still present, but much stronger fluorescence with an excitation wavelength of about 360 nm and a peak emission of about 455 nm is now evident. This wavelength combination is in accordance with FIG. 2.

Referring now to FIGS. 5 and 6, in the case of undamaged cotton boll tissue from the carpel wall, auto-fluorescence is exhibited with an optimum excitation peak wavelength of about 360 nm, and a peak emission peak wavelength of about 405 nm (FIG. 5). This peak is also present in tissue that has been fed on by a stink bug, as shown in FIG. 6. However, in the latter case a more intense peak with a peak excitation peak wavelength of about 460 nm is now present (FIG. 6). The matrix peaks shown in FIGS. 5 and 6 correspond to the spectral peaks shown in FIG. 2.

Figure 12:
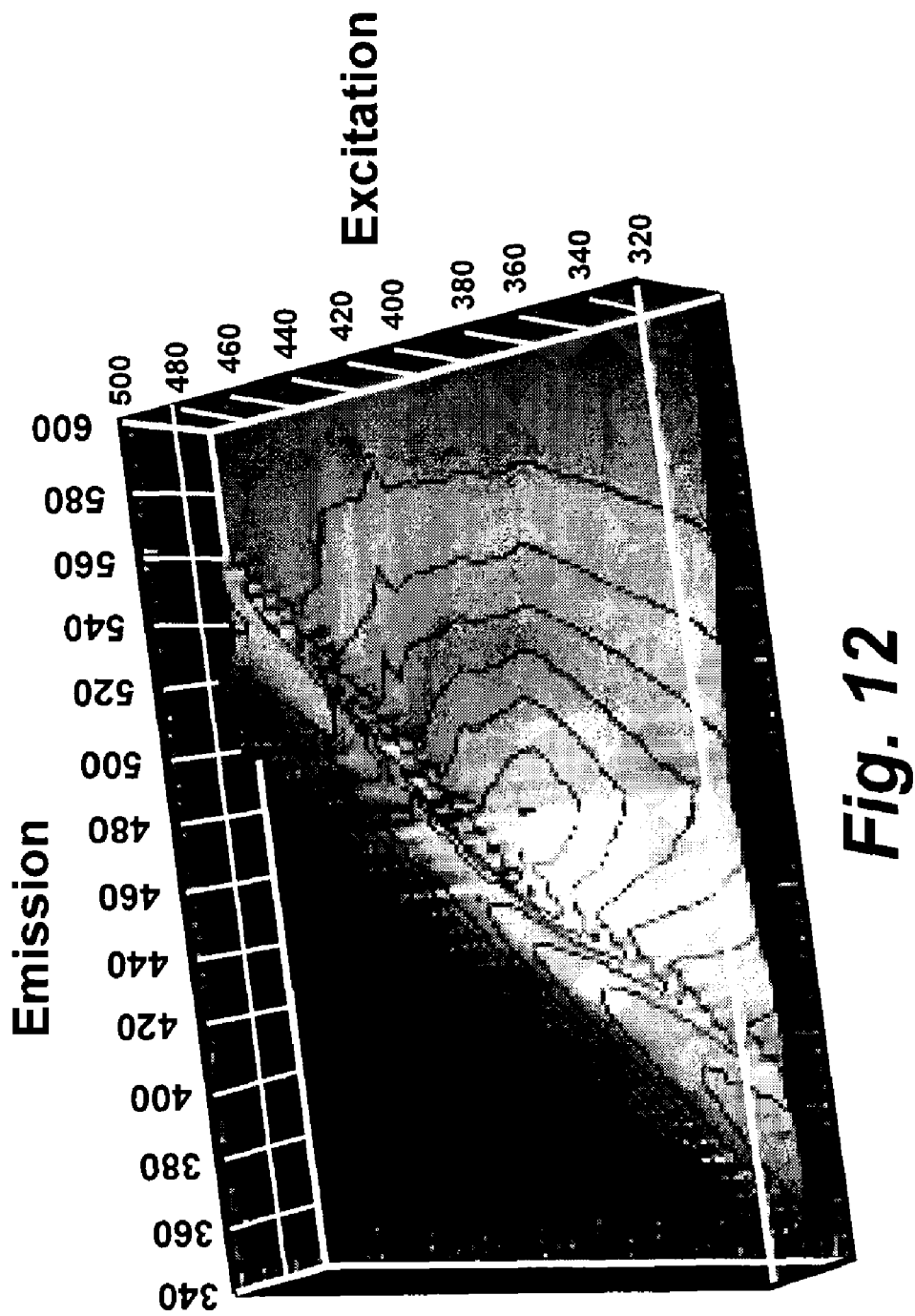
FIG. 12 illustrates the matrix scan for a normal sunflower seed.
Figure 13:
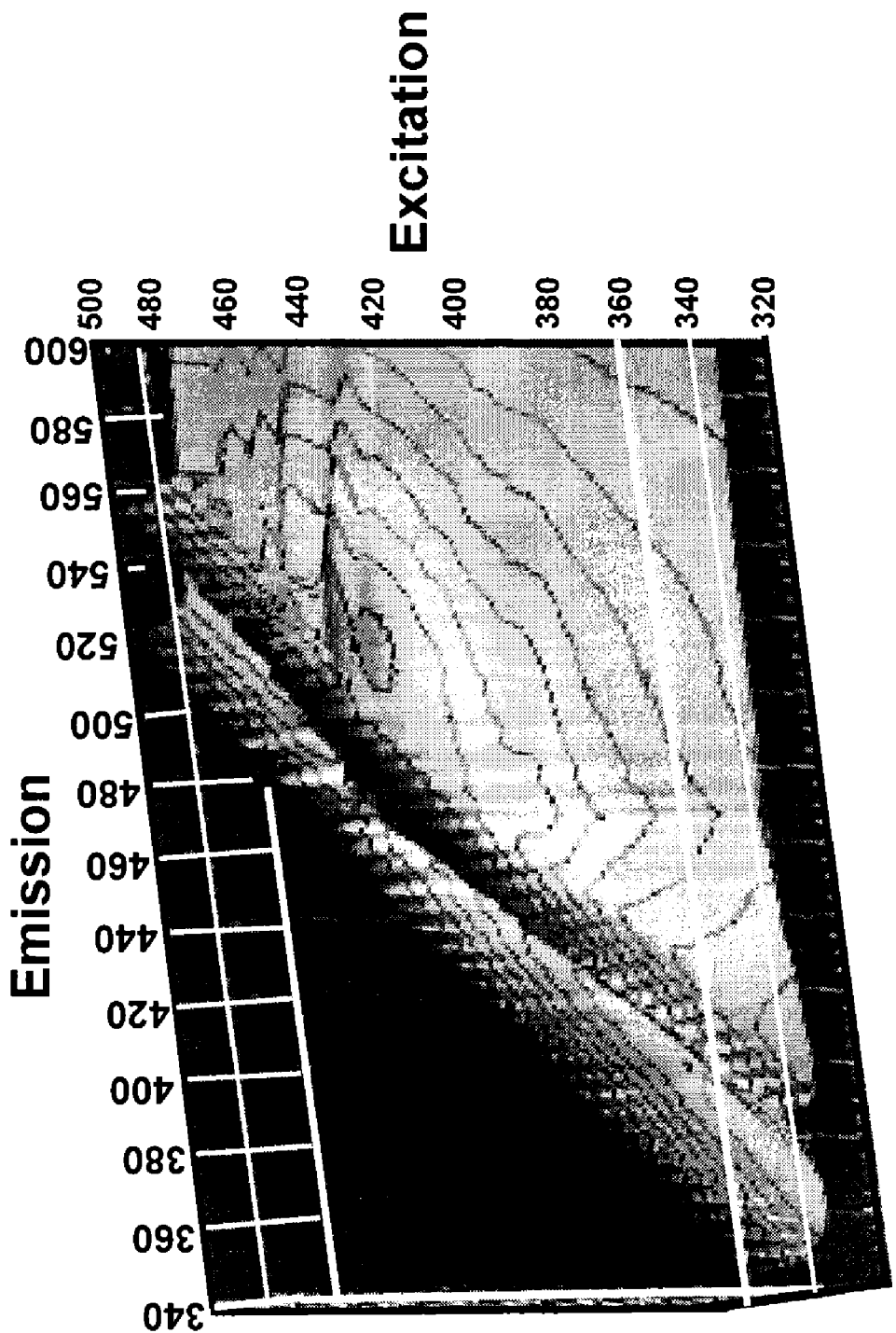
FIG. 13 illustrates the matrix scan for a sunflower seed damaged by stink bug.

Plant species other than cotton can require different excitation peak wavelengths and provide different emission spectra, compared to those associated with cotton. For example, referring now to FIGS. 12 and 13, undamaged sunflower seed tissue exhibits auto-fluorescence with an optimum excitation peak wavelength of about 405 nm and peak emission peak wavelength of about 465 nm (FIG. 12). This peak is also present in tissue that has been fed on by a stink bug (FIG. 6), However, with this plant subject a much stronger emission peak at a peak wavelength of about 515 nm is now present (FIG. 13).

Irrespective of the target plant species, a ratiometric measurement may be performed by illuminating the sample with a first ultraviolet or violet excitation light, and measuring the intensity of a first fluorescence emission intensity at a plant species-specific peak wavelength associated with healthy plant tissue (Intensity $I_1$). Next, the sample will be illuminated with a second ultraviolet or violet excitation light that may or may not be of the same peak wavelength as the first excitation light, and measuring the intensity of a second fluorescence emission intensity at a plant species-specific peak wavelength associated with insect-induced damaged plant tissue (Intensity $I_2$). Based on FIGS. 5 and 6, for example, the ratio $R=I_2/I_1$ will be less than 1 for undamaged plant tissue, and greater than 1 for damaged plant tissue. Computing a ratiometric measurement, such as R, may advantageously eliminate many effects that influence intensity such as distance of the light source and detector to the sample, tissue variations, or dust.

It is contemplated that a field-usable detection device provided according to the present disclosure may detect at least one fluorescent emission, excited with an ultraviolet or violet light of between about 350 nm to about 410 nm, that is indicative of an insect-induced plant tissue damage, and preferably provide numeric data and/or an image of the extent of the damage to the operator of the device measurement.

Figure 7:
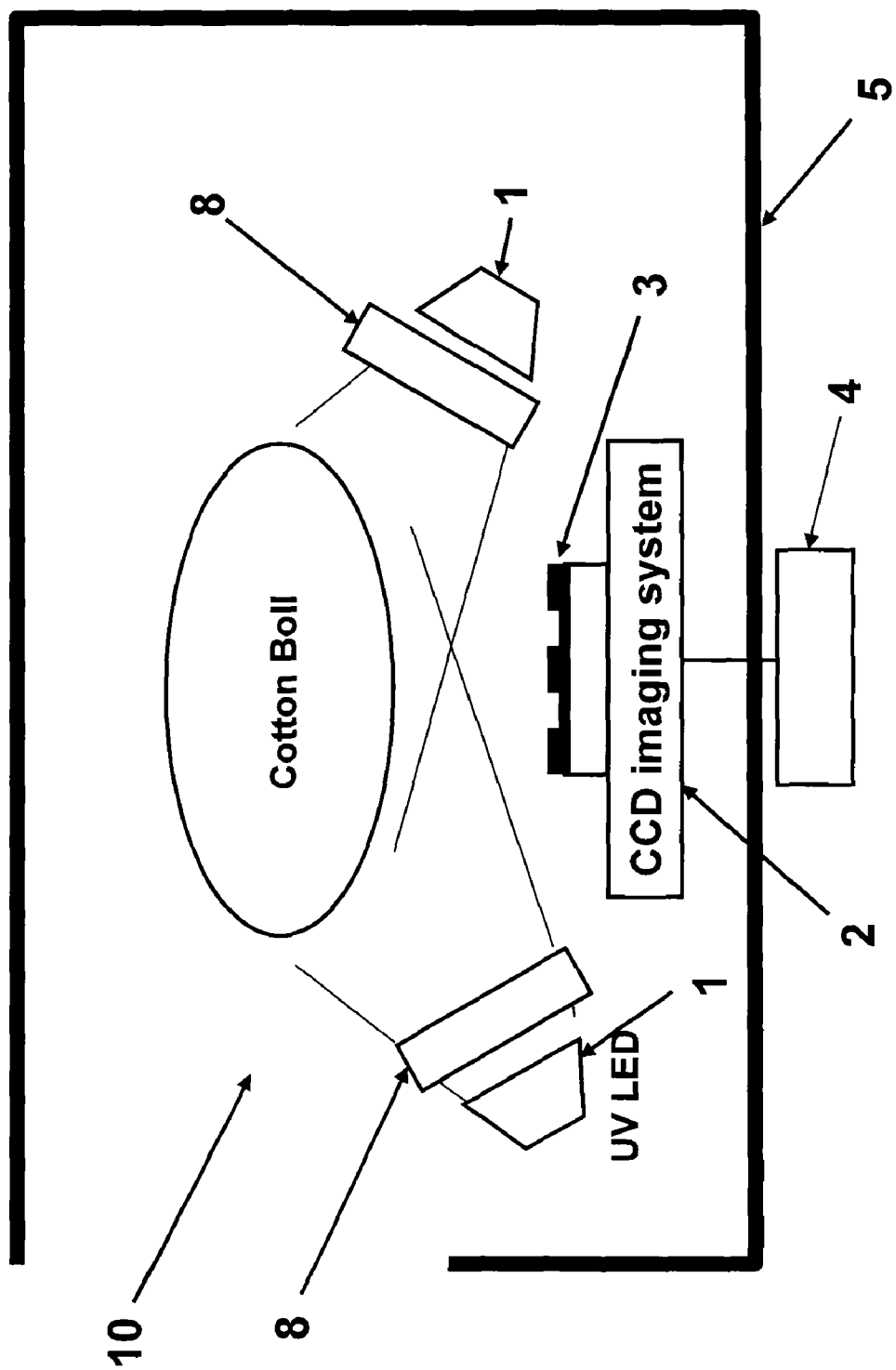
FIG. 7 illustrates an embodiment of a device for detecting insect-induced damage of a crop plant such as an intact cotton boll. Inside a light-attenuating enclosure 5 is a series of ultraviolet emitting LEDs 1 that may irradiate a plant or a fragment thereof with excitation light. A CCD or CMOS-based imaging system 2 detects the emitted fluorescence of the plant surface and indicates if insect damage is present.
Figure 8:
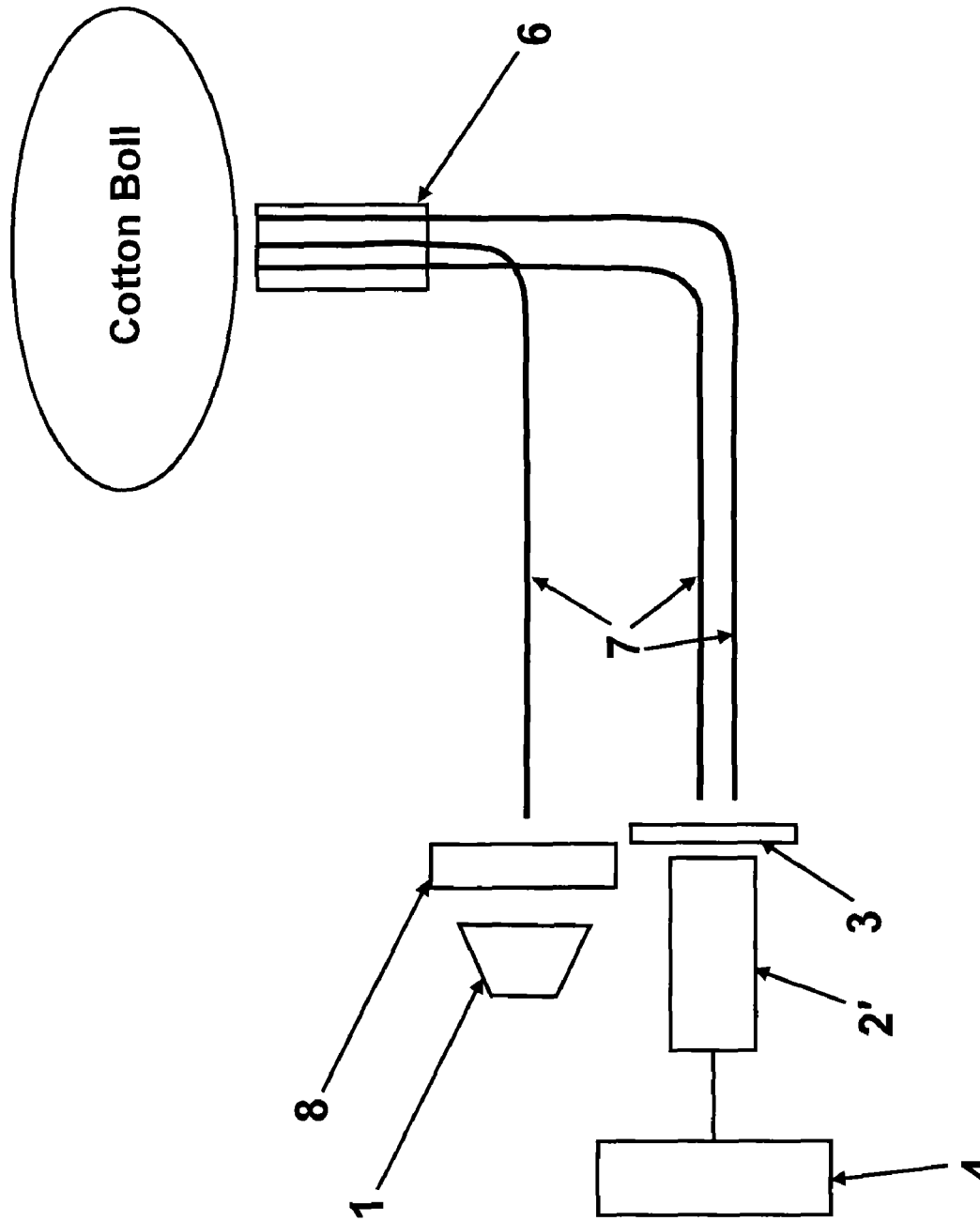
FIG. 8 illustrates an embodiment of a device for detecting insect-induced damage of a crop plant such as an intact cotton boll. In this embodiment, excitation and emission light may be conducted by flexible optical fibers. The fibers may be manipulated with a hand-held wand, and the operator moves the wand over the surface of the boll. Fluorescence emission may be detected with a photomultiplier tube (2), analyzed by a microprocessor-based system (4), and presented to the operator as an indication of insect-induced plant damage.
Figure 9A:
FIGS. 9A-9D show digital epifluorescence images of stink bug damaged cotton bolls.
Figure 9B:
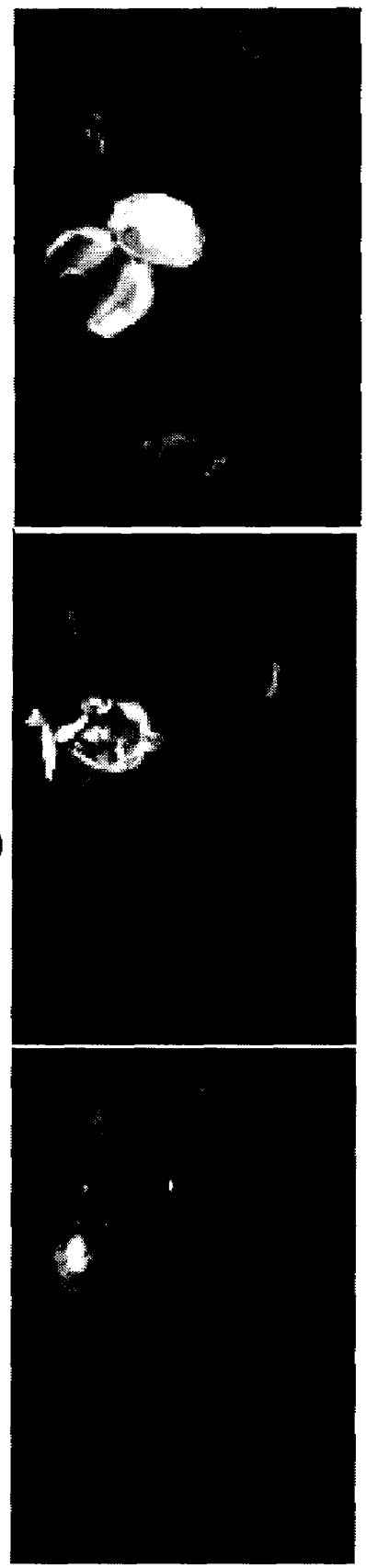
Figure 9C:
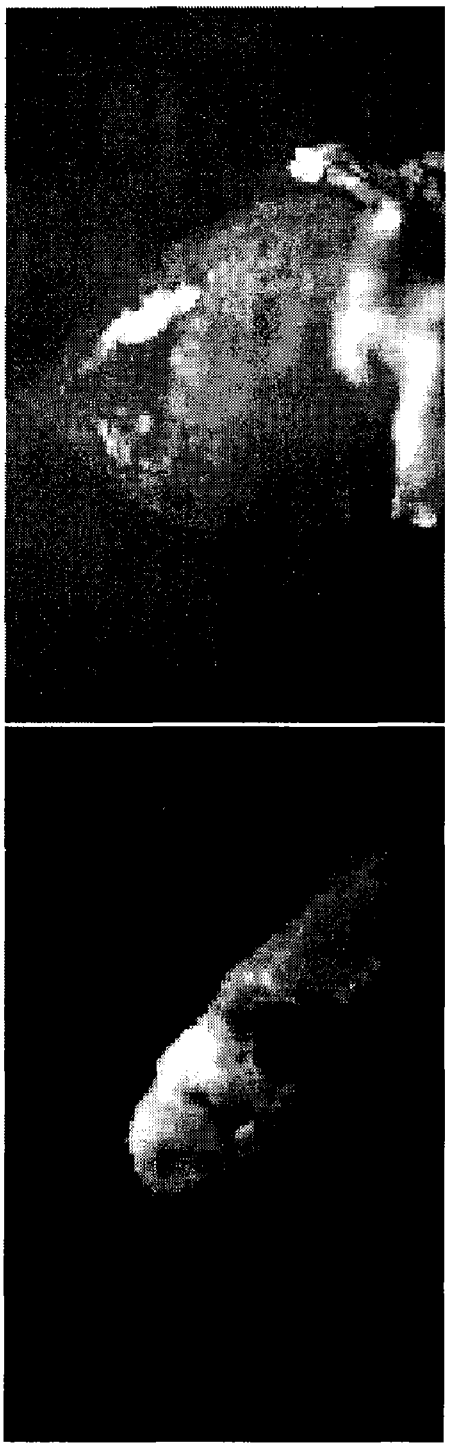
Figure 9D:
Figure 10:
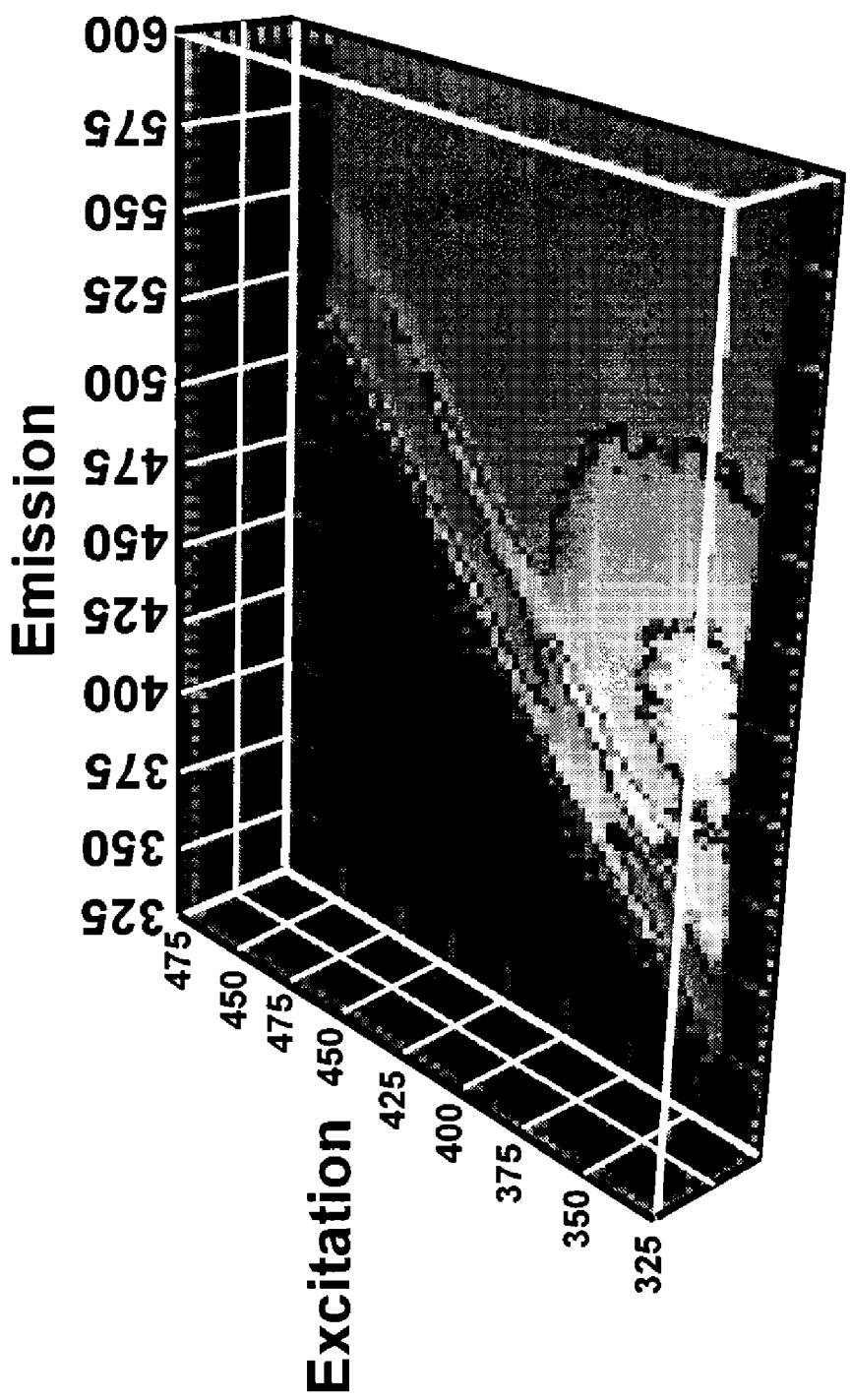
FIG. 10 shows a matrix spectroscopy scan of lesion material.
Figure 11:
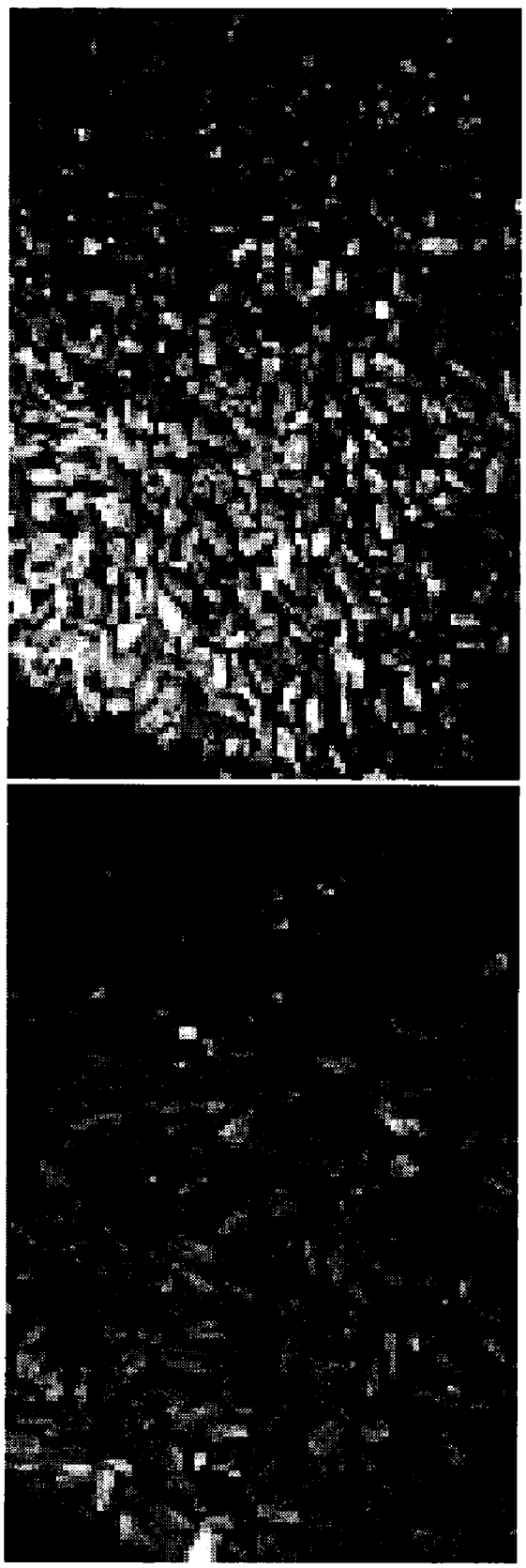
FIG. 11 shows an epifluorescence image of: left: undamaged sunflower seed; and right: damaged sunflower seed.
Figure 17:
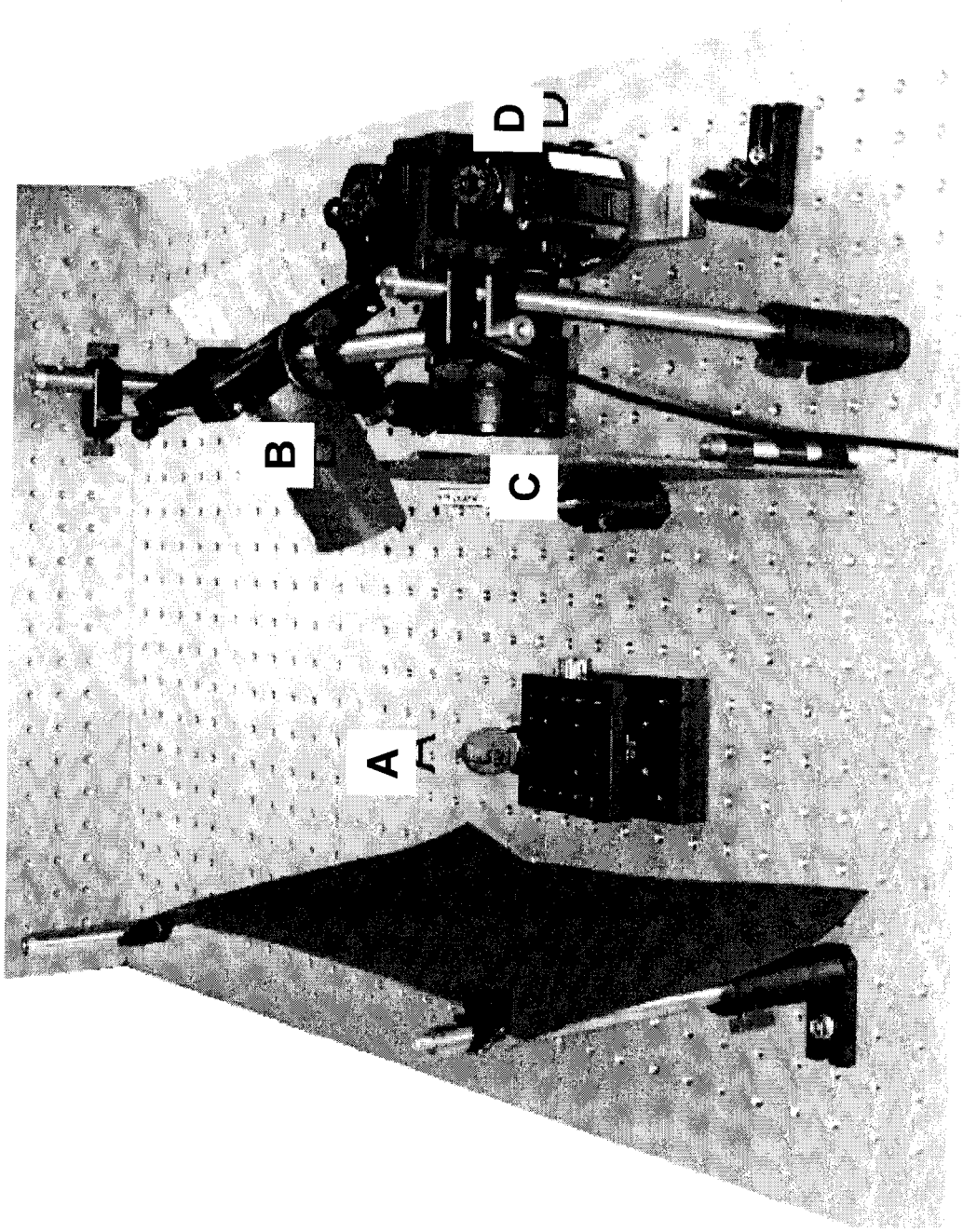
FIG. 17 is a digital image of a non-portable boll imaging apparatus. The boll sample (A) is placed on a rotary stage, which allows image acquisition from different angles. A near-UV light emitting diode array (B) provides excitation light and illuminates the sample with fluorescence-inducing UV light. The emission filter (C) eliminates UV excitation light in the emission path but allows blue fluorescence emission to pass. The fluorescent image is acquired with a SLR camera (D).

An aspect of the disclosure, therefore, provides is a portable device to detect insect-feeding damage of plant tissues. Embodiments of this aspect of the disclosure, as illustrated in FIGS. 7, 8 and 17, can comprise a source 1 of long-wavelength excitation light and an excitation filter 8, a light detector 2 configured to selectively detect a first fluorescence light, and optionally a second detector 2 configured to selectively detect a second fluorescence light. It is anticipated that the first and second light detectors 2 may be individual components or a single light detector having, for example, at least one filter 3 selected to allow passage of the light of the first or the second fluorescence to pass to the detector.

In embodiments of the devices of the present disclosure, the light source 1 may be any light source such an LED or LED array, a laser system and the like that emit a light having a wavelength suitable to excite the insect-induced fluorescence according to the methods herein. The light source 1 and the fluorescence light detector(s) 2 may be surrounded by an enclosure 5, the cross-section of which is illustrated in FIG. 7 that limits or excludes ambient light from the targeted plant or fragment thereof that is subject to the examination for insect damage. The enclosure and the assembled components of the systems 10 of the disclosure may be configured to provide a portable hand-held system 10 for examination of a plant or parts thereof in the field. In some embodiments, the devices may be configured to examine multiple target plants simultaneously, in which case the devices may not be hand-held.

It is anticipated that the light detector(s) 2 can be capable of emitting an electrical signal, the intensity or strength of the signal(s) being a function of the intensity of the light incident on the detector(s) 2. It is contemplated that the output signals from the detector(s) may be directed to an imaging component 4 to provide a direct visual representation, similar to those shown in FIG. 1, of the fluorescence emitted by the plant tissue exposed to the long-wavelength light of the methods of the disclosure. Alternatively, the electrical signal outputs from the light detectors 2 can be represented as numeric values by a means capable of converting the amplitude of the electrical signal into a quantitative numeric value, the magnitude of which is a function of the intensity of the output electrical signal. The devices of the disclosure may further comprise an electronic computational means 4 such as a microprocessor-based device to provide a ratiometric value for the intensities of the first fluorescence and the second fluorescence. The ratiometric value, as a numeric value may be presented to the operator who then assesses the value and determines whether insect-related damage is present on the tested plants. Alternatively, the device 10 converts the ratiometric value to a simple indication, such as, but not limited to, a light, a sound or a visual graphical representation indicating the presence of the insect-related plant damage.

In the devices of the present disclosure, it is anticipated that the devices may be portable and therefore able to be carried into a field for examination of a crop plant for an insect infestation as manifested by insect-induced fluorescence changes in the plant tissues. The excitation ultraviolet or violet light source, the fluorescent light detectors and the electronic circuitry for converting the electrical output signals from the detector(s) 2 may be operably connected in a unit or units small enough to be readily carried, and preferably hand-held. For the devices to be operable in daylight, the devices will preferably include a light shield enclosure 5 to enclose the target plant or fragment of a plant, thereby excluding ambient light from interfering with the incident and emitted lights of the test apparatus.

The microprocessor unit 4 of the devices 10 of the disclosure may analyze the spectral information and indicate to the operator whether or not insect damage is present. Two sensor unit embodiments for the detection device, while not intending to be limiting, are shown in FIGS. 7 and 8. Both embodiments are based on the principle that blue/ultraviolet excitation light may be guided to the plant surface, and emission light at different peak wavelengths is analyzed to identify the dominant emission peaks. Both devices preferably allow detection of insect damage without removing, breaking, or in other manner damaging the plant or part of the plant being tested. Light sources and detectors will be controlled by a microcontroller circuit, and data analysis takes place in a portable microprocessor unit attached to the detectors. The entire unit can be driven by conventional or rechargeable batteries. Optional optical, numeric data, acoustical signal, and the like may inform the operator of the presence of insect damage.

In one embodiment of the apparatus according to the disclosure, and shown in schematically in FIG. 8, the apparatus comprises a light channeling fiber optic 7 or a plurality of fiber optics, the distal ends of which are held in a stable configuration by a wand 6 that may be hand-held for holding against a target plant or part thereof, and the proximal ends of the fiber optics 7 are operably connected to the light source 1 or excitation filter 8 thereof, and to the fluorescence light detector 2.

In one embodiment of an apparatus employing the methods of the disclosure, insect damage detection may be achieved with a Line Scanner. To further automate and facilitate the detection process, it is contemplated that a CCD line scanner may be used as a fluorescence detector. A line scanner is an integrated circuit that typically contains 2,000 sensors in a linear array. Line scanners are often used in fax and desktop scanning devices and in electronic copiers.

Line scanners are useful for the reduction of the processing task to one-dimensional data processing which can be done by compact, handheld microcontroller devices. For example, a line scanner and two UV illumination arrays may be arranged in a drum large enough to fit over a cotton boll. The drum itself, or just the light source/fluorescence detector(s), then rotates around the cotton boll and gathers scan data that is analyzed for noise reduction, detection of cells with a high enough red signal, normalization of the blue signal against the red signal, and counting the number of cells with a blue to red ratio above a predetermined level. This number may be used as a metric for the determination of the amount of stinkbug feeding damage.

In addition to cotton bolls, sunflower seeds had a very similar spectral behavior and it is, therefore, anticipated that devices can be configured with regard especially for the wavelength of the excitation light and the fluorescence light associated with insect damage of a particular plant target such as cotton, sunflowers, corn, soybean, and various other plants affected by stink bugs and the like.

One aspect of the disclosure, therefore, encompasses methods of detecting insect-induced damage in a target plant tissue, comprising: (a) exposing a target plant or a fragment thereof, to an ultraviolet or violet light; and (b) detecting a first ultraviolet or violet light-induced fluorescence from the target plant or the fragment thereof, where a detectable level of fluorescence indicates the presence of insect-induced damage to the target plant or the fragment thereof.

In various embodiments of the disclosure, the method further comprises: (i) detecting a second ultraviolet or violet light-induced fluorescence from the target plant or the fragment thereof; (ii) measuring the levels of the intensities of the first and the second fluorescences; and (iii) determining the ratio of the level of intensity of the first ultraviolet or violet light-induced fluorescence to the level of the intensity of the second ultraviolet or violet light-induced fluorescence; whereby said ratio indicates the level of insect-damage to the plant or the fragment thereof.

In embodiments of this aspect of the disclosure, the target plant may be selected from the group consisting of: a leguminous crop, a grass crop, and a fruiting body crop.

In embodiments of this aspect of the disclosure, the target plant can be selected from the group consisting of: soybean, cowpea, corn, sorghum, rice, wheat, alfalfa, pecan, macadamia, apple, pear, cotton, and tomato, or a hybrid or variety thereof.

In some embodiments of this aspect of the disclosure, the target plant is selected from the group consisting of: a cotton plant, a sunflower plant, and a soybean plant.

In various embodiments of this aspect of the disclosure, the ultraviolet or violet excitation light has a peak wavelength of about 365 nm, the first ultraviolet or violet light-induced fluorescence has a peak wavelength of about 405 nm, and the second ultraviolet or violet light-induced fluorescence has a peak wavelength of about 465 nm, and wherein the target plant is a cotton plant, or a fragment thereof.

In some embodiments of this aspect of the disclosure, wherein the ultraviolet or violet excitation light has a peak wavelength of about 405 nm, and the first ultraviolet or violet light-induced fluorescence has a peak wavelength of about 465 nm, and the second ultraviolet or violet light-induced fluorescence has a peak wavelength of about 515 nm, and wherein the target plant is a sunflower plant, or a fragment thereof.

In embodiments of the methods of this aspect of the disclosure, a detectable level of fluorescence can indicate the presence of insect-induced damage to the target plant or fragment thereof by an insect of the order Hemiptera.

In some embodiments, the insect is a stink bug.

Another aspect of the disclosure encompasses devices configured for the identification of insect-induced damage in a plant or a fragment thereof, comprising: a source of an ultraviolet or violet light, wherein the wavelength thereof is selected to induce a fluorescence associated with insect-induced damage of a plant tissue; at least one light detector configured to provide an output electrical signal in response to a fluorescent light having a peak wavelength of about 405 nm to about 675 nm; an electronic system for converting the output electrical signal of the detector to a measurement of the intensity of the fluorescent light detected by the detector; and an output system for converting the measurement of the intensity of the fluorescent light detected by the detector to an indicator for indicating that a target plant or fragment thereof has insect-induced damage.

In embodiments of the apparatus of this aspect of the disclosure, the apparatus may further comprise an enclosure configured to receive a plant or a fragment thereof, and further configured to reduce ambient light around the plant or fragment thereof.

In embodiments of this aspect of the disclosure, the fluorescent light can have a peak wavelength selected from the group consisting of: about 405 nm, about 460 nm, about 515 nm, and about 675 nm, or a combination thereof.

In embodiments of this aspect of the disclosure, the measurement of the intensity of the fluorescent light may be displayed to an operator as a non-numeric indicator of the presence of insect-induced damage to a plant or a fragment thereof.

In some embodiments of this aspect of the disclosure, the measurement of the intensity of the fluorescent light can be displayed to an operator as a numeric value, wherein the numeric value indicates the presence of insect-induced damage to a plant or a fragment thereof.

In embodiments of this aspect of the disclosure, the source of an ultraviolet or violet light and the at least one light detector are disposed as a linear array, and wherein the apparatus is configured to allow the linear array to rotate around the axis of the target plant or fragment thereof.

In one embodiment of this aspect of the disclosure, wherein the source of an ultraviolet or violet light is configured to provide an ultraviolet or violet excitation light having a peak wavelength of about 365 nm, and the detector is configured to detect a first ultraviolet or violet light-induced fluorescence having a peak wavelength of about 405 nm, and a second ultraviolet or violet light-induced fluorescence having a peak wavelength of about 465 nm, and the target plant is a cotton plant, or a fragment thereof.

In another embodiments of this aspect of the disclosure, the source of an ultraviolet or violet light is configured to provide an ultraviolet or violet excitation light having a peak wavelength of about 405 nm, and the detector is configured to detect a first ultraviolet or violet light-induced fluorescence having a peak wavelength of about 465 nm, and a second ultraviolet or violet light-induced fluorescence having a peak wavelength of about 515 nm, and the target plant is a sunflower plant, or a fragment thereof.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

EXAMPLES

Example 1

Cotton lesion (tissue tumor, fluorescence material) was selectively cut and put to the micro-centrifuge tube mixed with water. The prepared sample was then frozen and then put at the room temperature for melting. When the sample was melted (solid sample/water mixture), sample was ground in a micro-centrifuge tube by a Teflon fluorocarbon resin pestle. The solution was isolated from the solid residue. Then the solution was loaded to a cuvette for excitation/emission spectroscopy measurement. The result, as presented in FIG. 2, showed that the cotton lesion has maximum emission intensity in the range of about 425 to about 475 nm with the excitation peak wavelength of about 350 nm.

Example 2

Sunflower Seed Study

FIG. 12 is the matrix scan for normal sunflower seed. The highest emission was about 465 nm with excitation peak wavelength of about 405 nm. This excitation/emission pair is the same as the infested cotton boll lesion material.

FIG. 13 is the matrix scan for sunflower seed infested by stink bug. Two prominent excitation peaks at 460 nm and 470 nm give emissions of about 510 to about 520 nm. This is the distinct point from the normal sunflower seed. From the figure, the normal sunflower seed excitation/emission finger print is also obvious (excitation 405 nm with emission 465 nm) although it's weaker compared to infested material. Therefore, sunflower seed stink bug-induced lesion inspection can use 465 nm excitation to detect 515 nm emission peak wavelength.

Figure 14A:
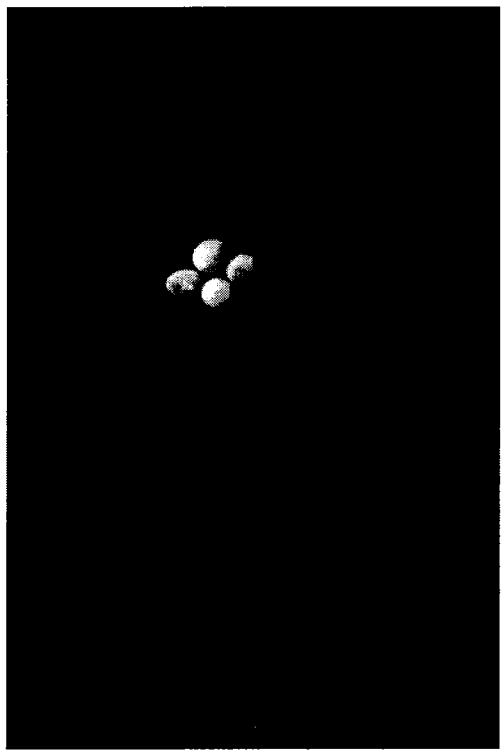
FIG. 14A is a digital image showing an epifluorescence image of damaged soybeans.
Figure 14B:
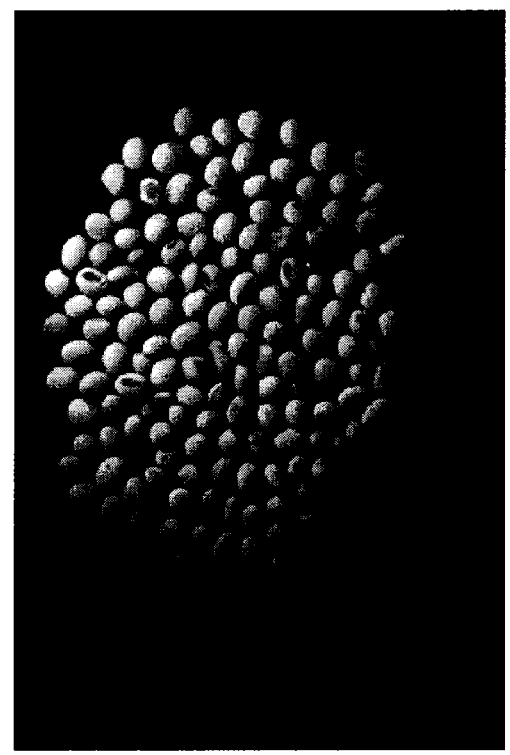
FIG. 14B is a digital image showing an epifluorescence image of undamaged soybeans.

The images shown in FIGS. 14A and 14B were taken using a standard camera with a 420 nm long pass filter in front of the camera lens. Soybeans were illuminated by a UV lamp. Stink bug damaged soybean shows a green-yellow fluorescence. In FIG. 14A, the small green-yellow spots were the feeding spots, distinguished from the larger and more homogeneous green-yellow background spots caused by the inhomogeneous illumination. In FIG. 14B, a large fluorescence not attributable to insect-related damage is located on upper-right part. The stink bug-induced damage fluorescence generally appeared as smaller spots.

Example 3

Stinkbug Damage Detection with CMOS Camera Chip

As shown in FIG. 17, a 390*nm* high-power LED was used as a UV light source to illuminate the cotton boll. The fluorescence image was taken by a standard digital SLR camera from above with a fixed 50 mm lens and a 480 nm long pass filter. The filter was used to cut off the short wave illumination light. The whole setup was shielded against bright environment light. All automatic features were disabled in the SLR camera, and settings were kept the same for all images to allow consistent quantitative image analysis. The recorded images were processed by the quantitative image analysis software "Crystal Image" (Haidekker Mass., Advanced Biomedical Image Analysis, Boston: Artech House 2010).

Figure 16B:
FIGS. 16A and 16B are digital images showing the effects of image processing. The images are the same as in FIGS. 15A and 15B. The images were segmented and normalized by using the red channel, and the resulting blue-red ratiometric value was false-colored. Stink bug feeding sites can be seen as bright spots (FIG. 16B) which are absent in FIG. 16A.
Figure 16A:
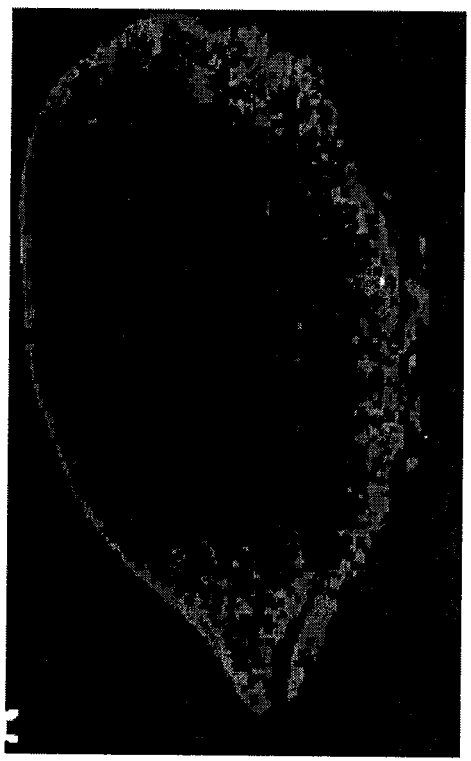

Each SLR raw image was converted to a 12 bit-per-pixel TIFF image and preprocessed by cropping, binning (4×4 pixels), and noise reduction through median and Gaussian filters. The red and blue channels were separated. The red channel was dominated by long-wave fluorescence caused by chlorophyll. Image intensity in the blue channel strongly depended on the presence of stink bug lesions. The red channel was therefore used to extract two elements of information: (1) the image area with the cotton boll (automated segmentation) and (2) illumination strength. By dividing the blue channel by the red channel, illumination inhomogeneities were attenuated. By using only the image region with high red emission, only the actual boll area was taken into consideration. Image processing results are shown in FIGS. 16A and 16B.

By simple thresholding or by histogram analysis, the relative area of bright (fluorescent) spots can be determined and used as a metric of stinkbug damage. A larger amount of these bright spots and—correspondingly—a larger relative indicated the presence of stinkbug feeding damage.

Example 4

An SLR camera with the capability to provide 12 bits per pixel resolution (digitization error less than 0.04%) was used in combination with a 365 nm LED light source and a 480 nm longpass emission filter. Bolls were placed on a rotary stage, which enabled acquisition of multiple images from different angles. The imaging setup is shown in FIG. 17.

From the SLR camera image, the red and blue channels were extracted. The red channel contained chlorophyll autofluorescence and served two purposes: identifying (segmenting) of the boll shape in the image and serving as an illumination reference. The blue channel, on the other hand, contained information about suspected stink bug feeding damage. Image processing steps were noise reduction, boll segmentation, computation of the normalized blue emission intensity (by computing the ratio of blue intensity to red intensity), and determination of the relative area of blue emission that exceeded a certain intensity threshold.

After the imaging process, all bolls were examined manually. Bolls were opened and visually inspected for the presence of any of three indicators, (a) lint staining, (b) formation of warts on the inner carpel wall, and (c) puncture marks. Presence of any of the three indicators classified the boll as "damaged". If all three indicators were absent the boll was classified as "undamaged".

Figure 18:
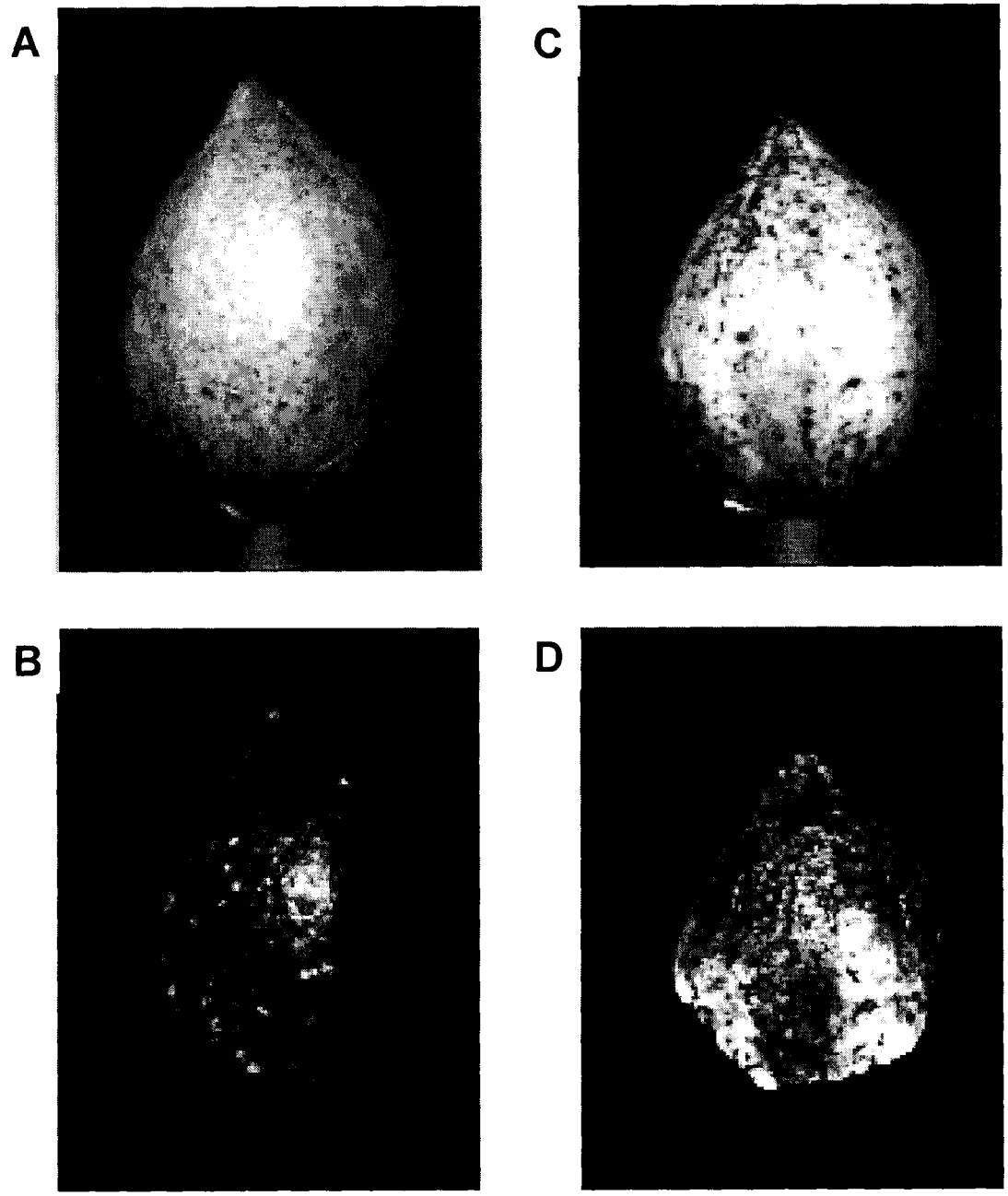
FIG. 18 shows a series of digital images of the comparison of the fluorescent images of an undamaged boll (A) and a damaged boll (C) that was identified to have developed warts and lint staining. The corresponding ratiometric images show much less blue emission in the undamaged case (B) compared to the damaged case (D).

FIG. 18 shows images from two sample bolls. Boll A was undamaged. A reddish tint can clearly be seen, which is indicative of chlorophyll fluorescence. The corresponding ratiometric image (blue relative to red) is shown in B. Boll C has been identified as having both warts and lint coloration. The unprocessed fluorescent image shows less red emission. The corresponding ratiometric image (D) is markedly brighter than (B), indicating a larger amount of blue fluorescent emission that is associated with stink bug damage.

Figure 19A:
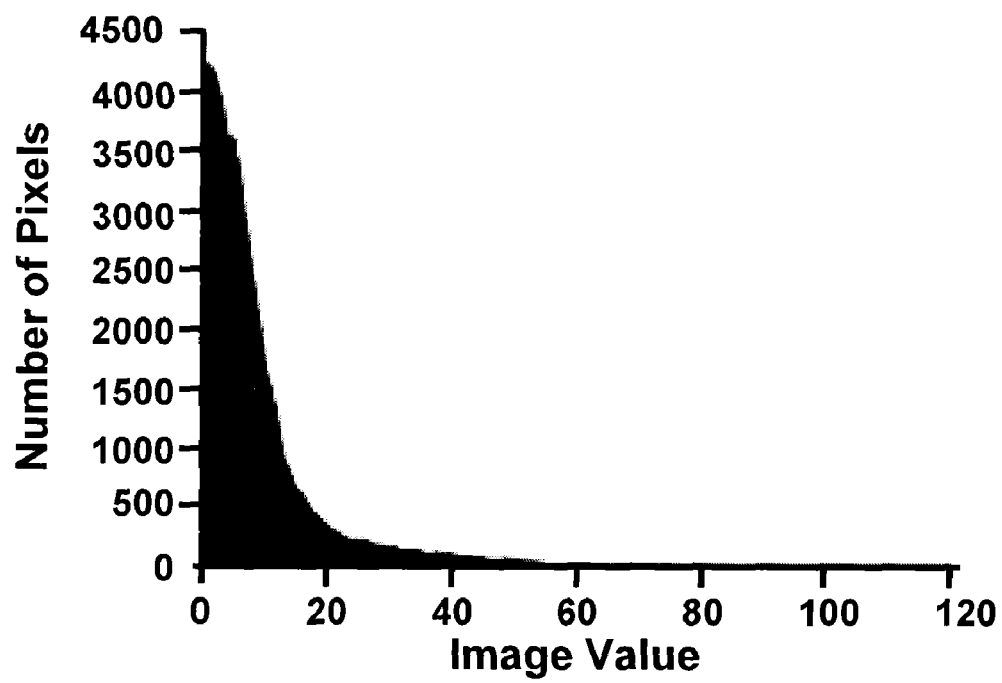
FIGS. 19A and 19B show intensity histograms obtained from the ratiometric images in FIG. 18. The histogram in FIG. 19A corresponds to the undamaged boll (FIG. 18, B), while the histogram in FIG. 19B) corresponds to the damaged boll (FIG. 18, D). A strong shift towards higher intensity values can be seen in the damaged case.
Figure 19B:
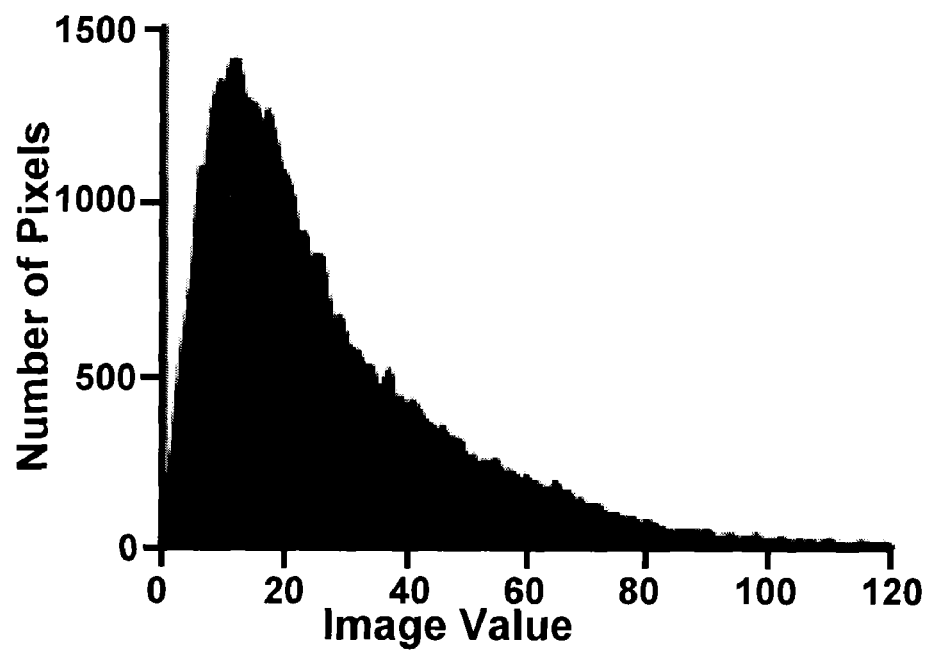

Intensity histograms that correspond to FIG. 18 (B and D) further highlight the difference. The intensity distribution in FIG. 18, D, reveals a higher probability of higher intensity values than the intensity distribution of the undamaged example (FIG. 18, B). The histograms (FIGS. 19A and 19B) allow to extract one single quantitative parameter, for example, the number of pixels that exceed an arbitrary, preselected threshold value or the intensity value that marks the highest 5% of the pixels.

In this specific example, 24 pixels above the value of 80 were found in the undamaged case, compared to 917 pixels in the damaged case. The 95% quantile is 29 in the undamaged case compared to 68 in the damaged case. Based on the manual examination, the image processing parameters (namely, threshold and quantile) can be selected to match the results obtained by manual examination.

Example 5

To test optical detection potential, undamaged and stink bug damaged bolls were prepared in the greenhouse. Cotton plants (FiberMax FM 9063 B2F) were grown under insect free conditions in 3-gallon pots. Starting at anthesis, nodes with first position white flowers were tagged. Fifteen days after anthesis, three $5^{th}$ instars of the southern green stink bug, *Nezara viridula*, (L.), were caged on each individual boll. Following three days of insect feeding, the bolls were harvested from the plant and analyzed.

Damaged and undamaged bolls were opened to examine differences in spectral properties under different types of light. The most striking visual result occurred when the bolls were viewed under UV lamp because the stink bug induced warts and stained lint glowed with green fluorescence (FIG. 1). To determine the exact wavelengths of excitation, parts of clean and stink bug damaged bolls were analyzed with fluorescence spectroscopy. These results (FIG. 2) showed that damaged bolls fluoresced at different wavelengths than non-damaged cotton bolls.

The internal and external surfaces of bolls were examined with low resolution epifluorescence microscopy. Regardless of the internal or external surface, the stink bug damaged bolls always exhibited blue-green fluorescence, whereas red chlorophyll autofluorescence was diminished. In contrast, undamaged bolls showed no sign of blue-green fluorescence but clear red chlorophyll fluorescence. This finding was even more encouraging because we were able to separate damaged and undamaged bolls without breaking them to expose the warts and stained lint. In fact, the blue-green fluorescence was strongly localized to where the mouthparts of the stink bug punctured the boll wall during feeding (FIG. 3) confirming that the differences in fluorescence appear to be linked with stink bug feeding.

We claim:
1. A method of detecting insect-induced damage in a target plant tissue, comprising:
    (a) exposing a target plant or a fragment thereof, to an ultraviolet or violet light;
    (b) detecting a first ultraviolet or violet light-induced fluorescence from the target plant or the fragment thereof; and
    (c) determining the presence of insect-induced damage to the target plant or the fragment thereof, whereby said presence is indicated by a detectable level of fluorescence.
2. The method of claim 1, further comprising:
    (i) detecting a second ultraviolet or violet light-induced fluorescence from the target plant or the fragment thereof;
    (ii) measuring the levels of the intensities of the first ultraviolet or violet light-induced fluorescence and the second ultraviolet or violet light-induced fluorescence; and
    (iii) determining the ratio of the level of intensity of the first ultraviolet or violet light-induced fluorescence to the level of the intensity of the second ultraviolet or violet light-induced fluorescence; whereby said ratio indicates the level of insect-damage to the plant or the fragment thereof.
3. The method of claim 2, wherein the ultraviolet or violet excitation light has a peak wavelength of about 365 nm, the first ultraviolet or violet light-induced fluorescence has a peak wavelength of about 405 nm, and the second ultraviolet or violet light-induced fluorescence has a peak wavelength of about 465 nm, and wherein the target plant is a cotton plant, or a fragment thereof.
4. The method of claim 2, wherein the ultraviolet or violet excitation light has a peak wavelength of about 405 nm, and the first ultraviolet or violet light-induced fluorescence has a peak wavelength of about 465 nm, and the second ultraviolet or violet light-induced fluorescence has a peak wavelength of about 515 nm, and wherein the target plant is a sunflower plant, or a fragment thereof.
5. The method of claim 1, wherein the target plant is selected from the group consisting of: a leguminous crop, a grass crop, and a fruiting body crop.
6. The method of claim 1, wherein the target plant is selected from the group consisting of: soybean, cowpea, corn, sorghum, rice, wheat, alfalfa, pecan, macadamia, apple, pear, cotton, and tomato, or a hybrid or variety thereof.
7. The method of claim 1, wherein the target plant is selected from the group consisting of: a cotton plant, a sunflower plant, and a soybean plant.

8. The method of claim 1, wherein a detectable level of fluorescence indicates the presence of insect-induced damage to the target plant or fragment thereof by an insect of the order Hemiptera.

9. The method of claim 1, wherein a detectable level of fluorescence indicates the presence of insect-induced damage to the target plant or fragment thereof by a stink bug.

10. An apparatus for the identification of insect-induced damage in a plant or a fragment thereof, comprising:
a source of an ultraviolet or violet light, wherein the wavelength thereof is selected to induce a fluorescence associated with insect-induced damage of a plant tissue;
at least one light detector configured to provide an output electrical signal in response to a fluorescent light having a peak wavelength of about 405 nm to about 675 nm;
an electronic system for converting the output electrical signal of the detector to a measurement of the intensity of the fluorescent light detected by the detector; and
an output system for converting the measurement of the intensity of the fluorescent light detected by the detector to an indicator for indicating that a target plant or fragment thereof has insect-induced damage.

11. The apparatus of claim 10, further comprising an enclosure, wherein the enclosure is configured to receive a plant or a fragment thereof, and further configured to reduce ambient light around the plant or fragment thereof.

12. The apparatus of claim 10, wherein the fluorescent light has a peak wavelength selected from the group consisting of: about 405 nm, about 460 nm, about 515 nm, and about 675 nm, or a combination thereof.

13. The apparatus of claim 10, wherein the measurement of the intensity of the fluorescent light is displayed to an operator as a non-numeric indicator of the presence of insect-induced damage to a plant or a fragment thereof.

14. The apparatus of claim 10, wherein the measurement of the intensity of the fluorescent light is displayed to an operator as a numeric value, wherein the numeric value indicates the presence of insect-induced damage to a plant or a fragment thereof.

15. The apparatus of claim 10, wherein the source of an ultraviolet or violet light and the at least one light detector are disposed as a linear array, and wherein the apparatus is configured to allow the linear array to rotate around the axis of the target plant or fragment thereof.

16. The apparatus of claim 10, wherein the source of an ultraviolet or violet light is configured to provide an ultraviolet or violet excitation light having a peak wavelength of about 365 nm, and the detector is configured to detect a first ultraviolet or violet light-induced fluorescence having a peak wavelength of about 405 nm, and a second ultraviolet or violet light-induced fluorescence having a peak wavelength of about 465 nm, and wherein the target plant is a cotton plant, or a fragment thereof.

17. The apparatus of claim 10, wherein the source of an ultraviolet or violet light is configured to provide an ultraviolet or violet excitation light having a peak wavelength of about 405 nm, and the detector is configured to detect a first ultraviolet or violet light-induced fluorescence having a peak wavelength of about 465 nm, and a second ultraviolet or violet light-induced fluorescence having a peak wavelength of about 515 nm, and wherein the target plant is a sunflower plant, or a fragment thereof.

* * * * *